(12) United States Patent
Andrews et al.

(10) Patent No.: US 10,768,143 B2
(45) Date of Patent: *Sep. 8, 2020

(54) METHODS OF CHARACTERIZING ION-EXCHANGED CHEMICALLY STRENGTHENED GLASSES CONTAINING LITHIUM

(71) Applicant: CORNING INCORPORATED, Corning, NY (US)

(72) Inventors: Ryan Claude Andrews, Elmira, NY (US); Rostislav Vatchev Roussev, Painted Post, NY (US); Vitor Marino Schneider, Painted Post, NY (US)

(73) Assignee: CORNING INCORPORATED, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/296,560

(22) Filed: Mar. 8, 2019

(65) Prior Publication Data
US 2019/0310228 A1 Oct. 10, 2019

Related U.S. Application Data

(63) Continuation of application No. 15/898,948, filed on Feb. 19, 2018, now Pat. No. 10,234,422, which is a
(Continued)

(51) Int. Cl.
*G01N 7/00* (2006.01)
*G01N 27/60* (2006.01)
(Continued)

(52) U.S. Cl.
CPC ........... *G01N 27/60* (2013.01); *C03C 21/002* (2013.01); *G01N 27/72* (2013.01); *G01N 33/386* (2013.01)

(58) Field of Classification Search
CPC ...... G01N 27/60; G01N 27/72; G01N 33/386; C03C 21/002
(Continued)

(56) References Cited

U.S. PATENT DOCUMENTS 5,117,469 A  5/1992  Cheung et al.
8,873,028 B2  10/2014  Sheldon et al.
(Continued)

OTHER PUBLICATIONS

English Translation of CN201680054449.3 Office Action dated Nov. 20, 2018; 7 Pages; Chinese Patent Office.
(Continued)

*Primary Examiner* — Max H Noori
(74) *Attorney, Agent, or Firm* — Kevin M. Johnson

(57) ABSTRACT

Methods of characterizing ion-exchanged chemically strengthened glass containing lithium are disclosed. The methods allow for performing quality control of the stress profile in chemically strengthened Li-containing glasses having a surface stress spike produced in a potassium-containing salt, especially in a salt having both potassium and sodium. The method allows the measurement of the surface compression and the depth of the spike, and its contribution to the center tension, as well as the compression at the bottom of the spike, and the total center tension and calculation of the stress at the knee where the spike and the deep region of the stress profile intersect. The measurements are for a commercially important profile that is near-parabolic in shape in most of the interior of the substrate apart from the spike.

14 Claims, 17 Drawing Sheets

Related U.S. Application Data continuation of application No. 15/267,392, filed on Sep. 16, 2016, now Pat. No. 9,897,574.

(60) Provisional application No. 62/219,949, filed on Sep. 17, 2015.

(51) Int. Cl.
*C03C 21/00* (2006.01)
*G01N 27/72* (2006.01)
*G01N 33/38* (2006.01)

(58) Field of Classification Search
USPC .......................................................... 73/763
See application file for complete search history.

(56) References Cited

U.S. PATENT DOCUMENTS

| | | | |
|---|---|---|---|
| 9,140,543 B1 | 9/2015 | Allan et al. | |
| 9,499,431 B2 | 11/2016 | Barefoot et al. | |
| 9,593,042 B2 | 3/2017 | Hu et al. | |
| 9,718,727 B2 | 8/2017 | Bookbinder et al. | |
| 2014/0092377 A1 | 4/2014 | Liu et al. | |
| 2014/0227524 A1 | 8/2014 | Ellison et al. | |
| 2014/0368808 A1 | 12/2014 | Roussev et al. | |
| 2015/0066393 A1 | 3/2015 | Liu et al. | |
| 2015/0079398 A1 | 3/2015 | Amin et al. | |
| 2015/0116713 A1 | 4/2015 | Roussev et al. | |
| 2015/0147574 A1* | 5/2015 | Allan | C03C 4/18 428/410 |
| 2015/0239775 A1 | 8/2015 | Amin et al. | |
| 2015/0338308 A1 | 11/2015 | Li et al. | |
| 2017/0121214 A1 | 5/2017 | Yamanaka et al. | |
| 2019/0194057 A1* | 6/2019 | Murayama | C03C 3/085 |

OTHER PUBLICATIONS

International Search Report and Written Opinion of the International Searching Authority; PCT/US2016/052045; dated Dec. 6, 2016; 11 Pages; European Patent Office.

Translation of JP2018514327 From Global Dossier dated Jun. 24, 2020; 6 Pages; Japanese Patent Office.

* cited by examiner

TABLE 1

| Time (Hours) | DOL spike (um) | CS (MPa) | CS Knee (MPa) | CT spike (MPa) | CS deep (MPa) | CT deep (MPa) | CT total (MPa) | DOC deep (um) | DOC total (um) |
|---|---|---|---|---|---|---|---|---|---|
| 1.1 | 6.67 | 484.85 | 181.45 | 3.2 | 204.81 | 102.4 | 105.6 | 169.06 | 165.45 |
| 1.1 | 6.62 | 495.33 | 186.04 | 3.23 | 209.75 | 104.88 | 108.11 | 169.06 | 165.5 |
| 1.1 | 6.65 | 486.36 | 190.06 | 3.11 | 214.17 | 107.09 | 110.2 | 169.06 | 165.71 |
| 1.1 | 6.61 | 494.27 | 183.17 | 3.25 | 206.55 | 103.27 | 106.52 | 169.06 | 165.43 |
| 1.1 | 6.61 | 497.64 | 183.17 | 3.28 | 206.6 | 103.3 | 106.58 | 169.06 | 165.39 |
| 1.1 | 6.62 | 481.12 | 176.85 | 3.18 | 199.51 | 99.76 | 102.94 | 169.06 | 165.38 |
| 1.1 | 6.56 | 496.22 | 175.7 | 3.32 | 198.23 | 99.11 | 102.43 | 169.06 | 165.19 |
| 1.1 | 6.6 | 490.89 | 172.26 | 3.32 | 194.52 | 97.26 | 100.58 | 169.06 | 165.12 |
| 1.1 | 6.6 | 495.69 | 176.72 | 3.29 | 202.76 | 101.38 | 104.67 | 169.06 | 165.31 |
| 1.1 | 6.62 | 483.7 | 177.43 | 3.2 | 200.19 | 100.09 | 103.3 | 169.06 | 165.37 |
| 1.1 | 6.62 | 483.7 | 177.43 | 3.2 | 200.19 | 100.09 | 103.3 | 169.06 | 165.37 |
| 1.1 | 6.62 | 479.52 | 178 | 3.15 | 200.77 | 100.38 | 103.54 | 169.06 | 165.43 |
| 1.1 | 6.63 | 478.72 | 178.58 | 3.14 | 201.43 | 100.72 | 103.86 | 169.06 | 165.46 |
| 1.1 | 6.64 | 482.28 | 180.87 | 3.16 | 204.02 | 102.01 | 105.17 | 169.06 | 165.48 |
| 1.1 | 6.6 | 482.54 | 173.41 | 3.22 | 195.67 | 97.84 | 101.06 | 169.06 | 165.26 |
| 1.1 | 6.59 | 475.17 | 176.28 | 3.11 | 198.72 | 99.36 | 102.47 | 169.06 | 165.44 |
| 1.1 | 6.58 | 484.14 | 172.26 | 3.24 | 194.36 | 97.18 | 100.42 | 169.06 | 165.21 |
| 1.1 | 6.62 | 478.72 | 178.58 | 3.14 | 201.37 | 100.69 | 103.82 | 169.06 | 165.46 |
| 1.1 | 6.61 | 483.08 | 180.3 | 3.16 | 203.29 | 101.64 | 104.8 | 169.06 | 165.47 |

FIG. 11

TABLE 3

| CS | DOL | CS$_k$ | pol | n$_0$ | n$_1$ | n$_2$ | n$_2$bir | CSn2 | ΔCSn2% | ΔCSn2% | dCSn2 |
|---|---|---|---|---|---|---|---|---|---|---|---|
| 675 | 9 | 95 | TE | 1.50818 | 1.50597 | 1.50421 | 0.00105 | 348.2 | 0.0 | 0.00 | 0.00 |
| 675 | 9 | 95 | TM | 1.50998 | 1.50738 | 1.50526 | | | | | |
| 675 | 9 | 85 | TE | 1.50833 | 1.50609 | 1.50430 | 0.00103 | 342.7 | -5.5 | -1.57 | 0.55 |
| 675 | 9 | 85 | TM | 1.51011 | 1.50748 | 1.50533 | | | | | |
| 675 | 9 | 105 | TE | 1.50803 | 1.50586 | 1.50413 | 0.00107 | 353.3 | 5.2 | 1.48 | 0.52 |
| 675 | 9 | 105 | TM | 1.50986 | 1.50729 | 1.50519 | | | | | |
| 625 | 9 | 95 | TE | 1.50770 | 1.50562 | 1.50400 | 0.00093 | 308.7 | -39.4 | -11.33 | 0.79 |
| 625 | 9 | 95 | TM | 1.50937 | 1.50692 | 1.50493 | | | | | |
| 725 | 9 | 95 | TE | 1.50867 | 1.50633 | 1.50445 | 0.00116 | 384.8 | 36.6 | 10.51 | 0.73 |
| 725 | 9 | 95 | TM | 1.51060 | 1.50785 | 1.50561 | | | | | |
| 675 | 8.6 | 95 | TE | 1.50809 | 1.50581 | 1.50403 | 0.00099 | 326.5 | -21.7 | -6.24 | 54.30 |
| 675 | 8.6 | 95 | TM | 1.50988 | 1.50720 | 1.50502 | | | | | |
| 675 | 9.4 | 95 | TE | 1.50827 | 1.50612 | 1.50439 | 0.00110 | 364.6 | 16.4 | 4.71 | 40.98 |
| 675 | 9.4 | 95 | TM | 1.51008 | 1.50756 | 1.50549 | | | | | |

FIG. 13

METHODS OF CHARACTERIZING ION-EXCHANGED CHEMICALLY STRENGTHENED GLASSES CONTAINING LITHIUM

CROSS-REFERENCE TO RELATED APPLICATIONS

This application is a continuation of U.S. patent application Ser. No. 15/898,948 filed on Feb. 19, 2018 which, is a continuation of U.S. patent application Ser. No. 15/267,392, filed on Sep. 16, 2016, which claims the benefit of priority to U.S. Provisional Patent Application Ser. No. 62/219,949, filed on Sep. 17, 2015, and which is incorporated by reference herein.

FIELD

The present disclosure relates to chemically strengthened glass, and in particular relates to methods of characterizing ion-exchanged chemically glasses containing lithium.

BACKGROUND

Chemically strengthened glasses are glasses that have undergone a chemical modification to improve at least one strength-related characteristic, such as hardness, resistance to fracture, etc. Chemically strengthened glasses have found particular use as cover glasses for display-based electronic devices, especially hand-held devices such as smart phones and tablets.

In one method, the chemical strengthening is achieved by an ion-exchange process whereby ions in the glass matrix are replaced by externally introduced ions, e.g., from a molten bath. The strengthening generally occurs when the replacement ions are larger than the native ions (e.g., Na+ ions replaced by K+ ions). The ion-exchange process gives rise to a refractive index profile that extends from the glass surface into the glass matrix. The refractive index profile has a depth-of-layer or DOL that defines a size, thickness or "deepness" of the ion-diffusion layer as measured relative to the glass surface. The refractive index profile also defines a number of stress-related characteristics, including a stress profile, a surface stress, center tension, birefringence, etc. The refractive index profile defines an optical waveguide when the profile meets certain criteria.

Recently, chemically strengthened glasses with a very large DOL (and more particularly, a large depth of compression) have been shown to have superior resistance to fracture upon face drop on a hard rough surface. Glasses that contain lithium ("Li-containing glasses") can allow for fast ion exchange (e.g., Li+ exchange with Na+ or K+) to obtain a large DOL. Substantially parabolic stress profiles are easily obtained in Li-containing glasses, where the ion-exchange concentration profile of Na+ connects in the central plane of the substrate, shrinking the traditional central zone of the depth-invariant center tension to zero or negligible thickness. The associated stress profiles have a predictable and large depth of compression, e.g., on the order of 20% of the sample thickness, and this depth of compression is quite robust with respect to variations in the fabrication conditions.

A stress profile of particular commercial importance is a near-parabolic (substantially parabolic) profile that has a "spike" near the surface. The transition between the parabolic portion of the profile and the spike has a knee shape. The spike is particularly helpful in preventing fracture when the glass is subjected to force on its edge (e.g., a dropped smart phone) or when the glass experiences significant bending. The spike can be achieved in Li-containing glasses by ion exchange in a bath containing $KNO_3$. It is often preferred that the spike be obtained in a bath having a mixture of $KNO_3$ and $NaNO_3$ so that Na+ ions are also exchanged. The Na+ ions diffuse faster than K+ ions and thus diffuse at least an order of magnitude deeper than the K+ ions. Consequently, the deeper portion of the profile is formed mainly by Na+ ions and the shallow portion of the profile is formed mainly by K+ ions.

In order for chemically strengthened Li-containing glasses to be commercially viable as cover glasses and for other applications, their quality during manufacturing must be controlled to certain specifications. This quality control depends in large part on the ability to control the ion-exchange process during manufacturing, which requires the ability to quickly and non-destructively measure the refractive index (or stress) profiles, and particular the stress at the knee portion, called the "knee stress."

Unfortunately, the quality control for glasses with spike stress profiles is wanting due to the inability to adequately characterize the profiles in a non-destructive manner. This inability has made manufacturing of chemically strengthened Li-containing glasses difficult and has slowed the adoption of chemically strengthened Li-containing glasses in the market.

SUMMARY

An aspect of the disclosure is directed to methods of characterizing chemically strengthened Li-containing glasses having a surface stress spike, such as produced by an ion-exchange process (i.e., an in-diffusion of alkali ions) whereby in an example Li+ is exchanged with K+ and Na+ ions (i.e., Li+⇔K+, Na+). The methods result in a measurement of the surface compression and the depth of the spike, and its contribution to the center tension, as well as the compression at the bottom of the spike, and the total center tension.

The method is preferably carried out to obtain a commercially important stress profile, e.g., one that is near-parabolic in shape in most of the interior of the substrate other than the spike adjacent the substrate surface. The spike is generally formed by the slower diffusion (and thus shallower) K+ ions while the substantially parabolic portion is formed by the faster (and thus deeper) diffusing Na+ ions. The method allows for confirmation that the profile has reached the near-parabolic regime, e.g., has a self-consistency check. The method can also include performing quality control of the glass samples being process. Such quality control is important for a commercially viable manufacturing process.

The present disclosure provides a method for quality control of the stress profile in chemically strengthened Li-containing glasses having a surface stress spike produced in a potassium-containing salt, especially in a salt having both potassium and sodium. The method allows the measurement of the surface compression and the depth of the spike, and its contribution to the center tension, as well as the compression at the bottom of the spike, and the total center tension, for a commercially important profile that is near-parabolic in shape in most of the interior of the substrate (apart from the spike). The method allows to check that the profile has reached the near-parabolic regime, e.g., has a self-consistency check. The method provides a critically important tool for the quality control that is necessary for the adoption of lithium-containing glasses that allow the fabrication of these important profiles.

Prior art methods of measuring the stress level at the bottom of the spike (i.e., the knee stress) are limited by the relatively poor precision of measuring the position of the critical-angle transition of the transverse electric (TE) angular coupling spectrum. This poor precision is an inherent aspect of the TE transition, which is broad and hence appears blurred in the prism-coupling spectra. This lack of sharpness causes the measured position of the mode lines to be susceptible to interference from nun-uniformity in the angular distribution of the illumination (e.g., background non-uniformity), as well as simply image noise.

Several of the methods disclosed herein avoid the need to measure the position of the critical-angle of the TE transition precisely. In one aspect of the method, the surface stress and the slope of the stress in the spike are measured, as well as the depth (depth-of-layer, or DOL) of the spike, where the DOL is measured very precisely by using only the critical-angle transition of the TM wave. This TM transition is sharper than the TE transition and thus allows for a much more precise measurement. Thus, in an example of the method, the TE mode spectrum (and in particular the TE transition of the TE spectrum) is not used to determine the DOL of the spike.

Knowing the surface stress and slope of the spike, and the depth of the spike (the aforementioned DOL), the stress at the bottom of the spike is determined, where the bottom of the spike occurs at the depth=DOL. This is the "knee stress" and is denoted herein as either $CS_{knee}$ or $CS_k$ or in the more general form $\sigma_{knee}$. The rest of the calculation of the stress profile attributes then proceeds according to the prior art method.

A second method disclosed herein avoids a direct measurement of the knee stress and calculates the knee stress by using the birefringence of the last guided mode common to both the TM and the TE polarization, and a previously determined relationship between the birefringence of said last common guided mode and the stress at the knee. Advantage is taken of the generally better precision of measurement of the mode positions in comparison to the precision of measurement of critical angle, and in particular of the critical angle of the TE wave in the case of spiked deep profiles in a Li-containing glass.

Advantages of the methods disclosed herein is that they are non-destructive and can carried out with high-throughput and with high precision to determine the critical parameters associated with the diffusion process in making chemically strengthened glasses. These critical parameters include CS, depth of spike, estimate of the compression depth, and frangibility status (based on an estimate of CT that is provided by the method). Another advantage is that the methods can be implemented with relatively modest software enhancements on existing hardware used for quality control of the currently produced chemically strengthened glasses.

One major specific advantage of the new methods disclosed herein is a significant improvement in the precision of the knee-stress estimate by avoiding the effects of large errors in the direct measurement of the TE critical angle. This precision improvement is important because it allows for improved quality control of the chemically strengthened glass product.

The other advantage of the methods disclosed herein is an increase in domain of applicability of the methods, i.e., an increase in the size of the measurement process window. The prior art methods have process windows or "sweet spots" for making measurements, where there was no leaky mode occurring in the vicinity of the critical-angle transition for the TM and TE spectra. Such a leaky mode causes significant deformation of the angular distribution of intensity in the vicinity of the transition, and is a source of very significant and unacceptable errors that are difficult to eliminate or effectively compensate for in realistic situations.

In the first of the new methods, only the TM spectrum is required to be free of leaky-mode interference, which on average doubles the range of the sweet spot.

In both of the new methods, the effect of errors in the critical-angle measurement is significantly reduced because the critical angle is not used for a direct measurement of the knee stress. This leads to an effective increase in the range of the sweet spot.

Additional features and advantages are set forth in the Detailed Description that follows, and in part will be readily apparent to those skilled in the art from the description or recognized by practicing the embodiments as described in the written description and claims hereof, as well as the appended drawings. It is to be understood that both the foregoing general description and the following Detailed Description are merely exemplary, and are intended to provide an overview or framework to understand the nature and character of the claims.

BRIEF DESCRIPTION OF THE DRAWINGS

The accompanying drawings are included to provide a further understanding, and are incorporated in and constitute a part of this specification. The drawings illustrate one or more embodiment(s), and together with the Detailed Description serve to explain principles and operation of the various embodiments. As such, the disclosure will become more fully understood from the following Detailed Description, taken in conjunction with the accompanying Figures, in which:

FIG. 11 sets forth a Table 1 that shows the computation of profile parameters for a number of different glass samples;

FIG. 13 shows a Table 3 that includes the calculated effective indices of the 3 guided modes for both the TM and TE polarizations for several different assumed values of $CS_k$, CS, and DOL for an example waveguide formed in a glass substrate;

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute part of this Detailed Description.

Figure 1A:
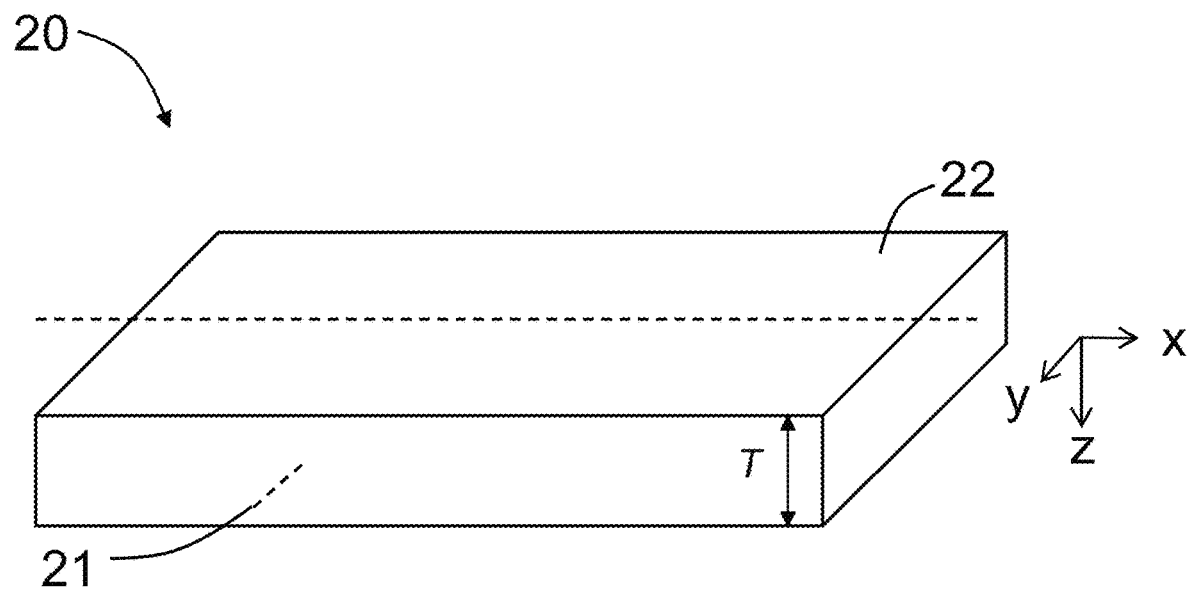
FIG. 1A is an elevated view of an example DIOX glass substrate in the form of a planar substrate.
Figure 1B:
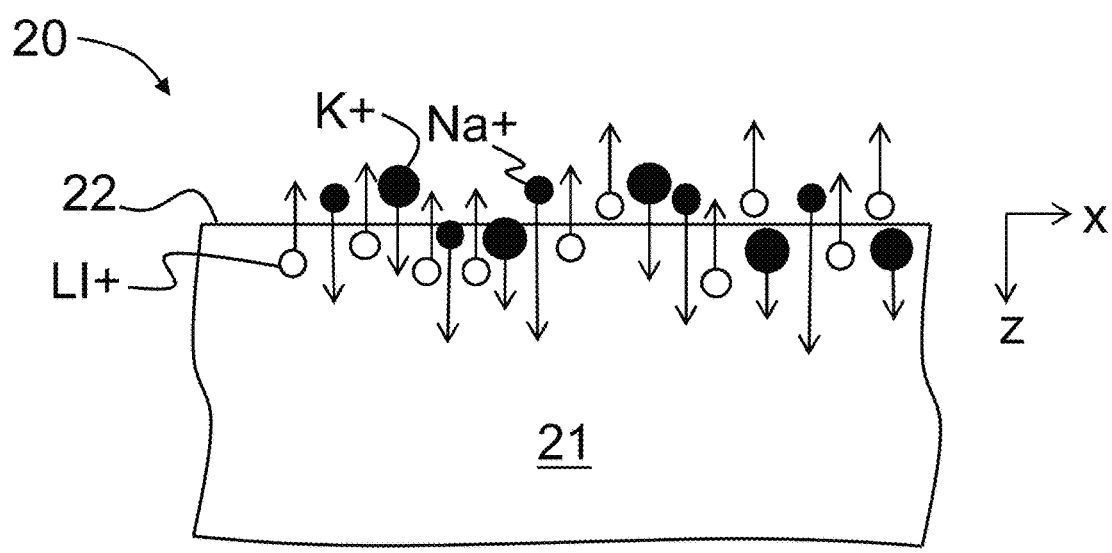
FIG. 1B is a close-up cross-sectional view of the DIOX substrate of FIG. 1A as taken in the x-z plane and that illustrates the double ion-exchange process that takes place across the substrate surface and into the body of the substrate.

FIG. 1A is an elevated view an example glass substrate in the form of a planar ion-exchanged substrate 20 that has a body 21 and a (top) surface 22, wherein the body has a base (bulk) refractive index $n_s$, a surface refractive index $n_0$ and a thickness T in the z-direction. FIG. 1B is a close-up cross-sectional view of ion-exchanged substrate 20 as taken in the y-z plane and illustrates an example double ion-exchange (DIOX) process that takes place across surface 22 and into body 21 in the z-direction.

In the DIOX process discussed in connection the method disclosed herein, two different types of ions Na+ and K+ replace another different ion Li+ that is part of the glass body 21. The Na+ and K+ ions can be introduced into the glass body 21 either sequentially or concurrently using known ion-exchange techniques. As noted above, the Na+ ions diffuse faster than the K+ ions and thus go deeper into the glass body 21. This has an effect on the resulting refractive index profile and stress profile, as discussed below.

Figure 1C:
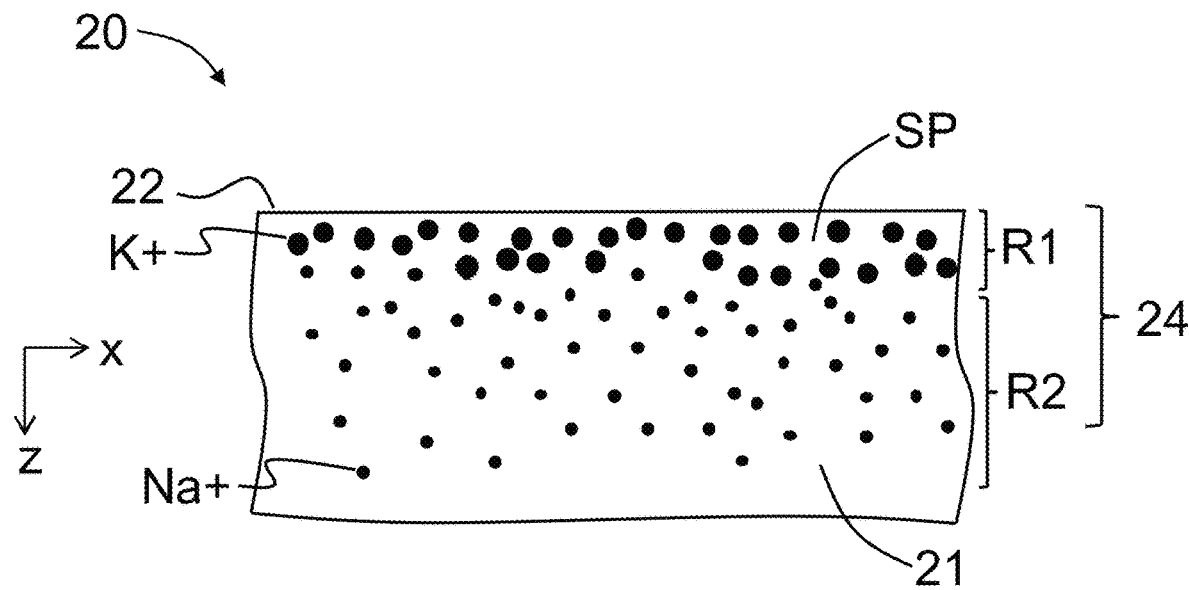
FIG. 1C schematically illustrates the result of the DIOX process that forms the DIOX substrate.
Figure 2:
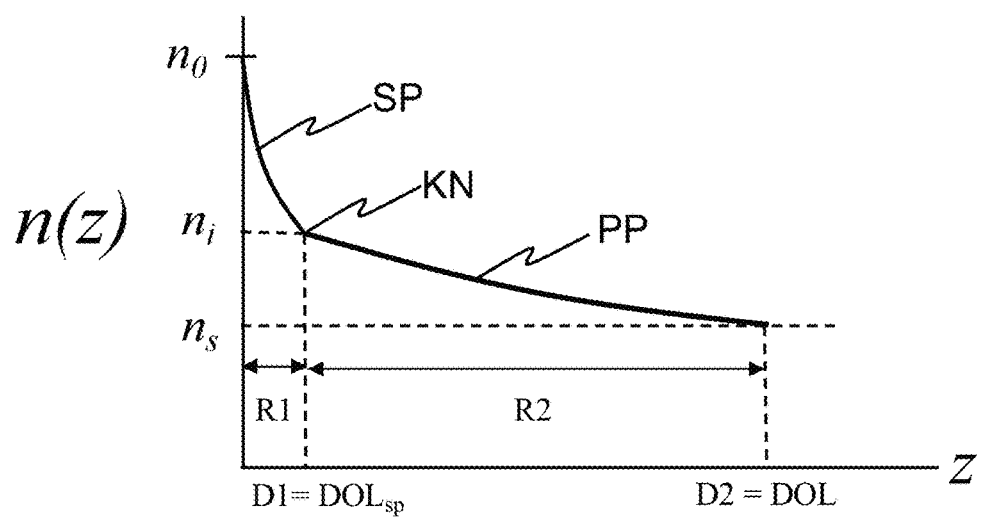
FIG. 2 is a representation of an example refractive index profile n(z) for the DIOX substrate illustrated in FIG. 1C.

FIG. 1C is a schematic diagram of the resulting DIOX process, and FIG. 2 is a representation of an example refractive index profile n(z) for substrate 20 having undergone the DIOX process and having a refractive index profile such as illustrated in FIG. 1C. The corresponding stress profile can be represented by σ(z). The refractive index profile n(z) includes a first "spike" SP associated with a region R1 associated with the shallower ion-exchange (K+ ions) and that has a depth D1 into body 21 that defines a "depth-of-layer for the spike" also denoted hereinafter as $DOL_{sp}$. The refractive index profile n(z) also includes a second region R2 associated with the deeper ion-exchange (Na+ ions) and that has a depth D2 that defines the depth-of-layer (DOL) and also denoted $DOL_p$. In an example, the portion of the refractive index profile n(z) in second region R2 is denoted PP because it has a parabolic shape or generally a power-law shape. The spike SP and power-law profile PP intersect at a location KN that has the shape of a knee.

The deeper second region R2 may be produced in practice prior to the shallower region. The region R1 is adjacent substrate surface 22 and is relatively steep and shallow, whereas region R2 is less steep and extends relatively deep into the substrate to the aforementioned depth D2. In an example, region R1 has a maximum refractive index $n_0$ at substrate surface 22 and steeply tapers off to an intermediate index $n_i$, while region R2 tapers more gradually from the intermediate index down to the substrate (bulk) refractive index $n_s$. The portion of the refractive index profile n(z) for region R1 represents spike SP in the refractive index having a depth DOS.

Figure 3A:
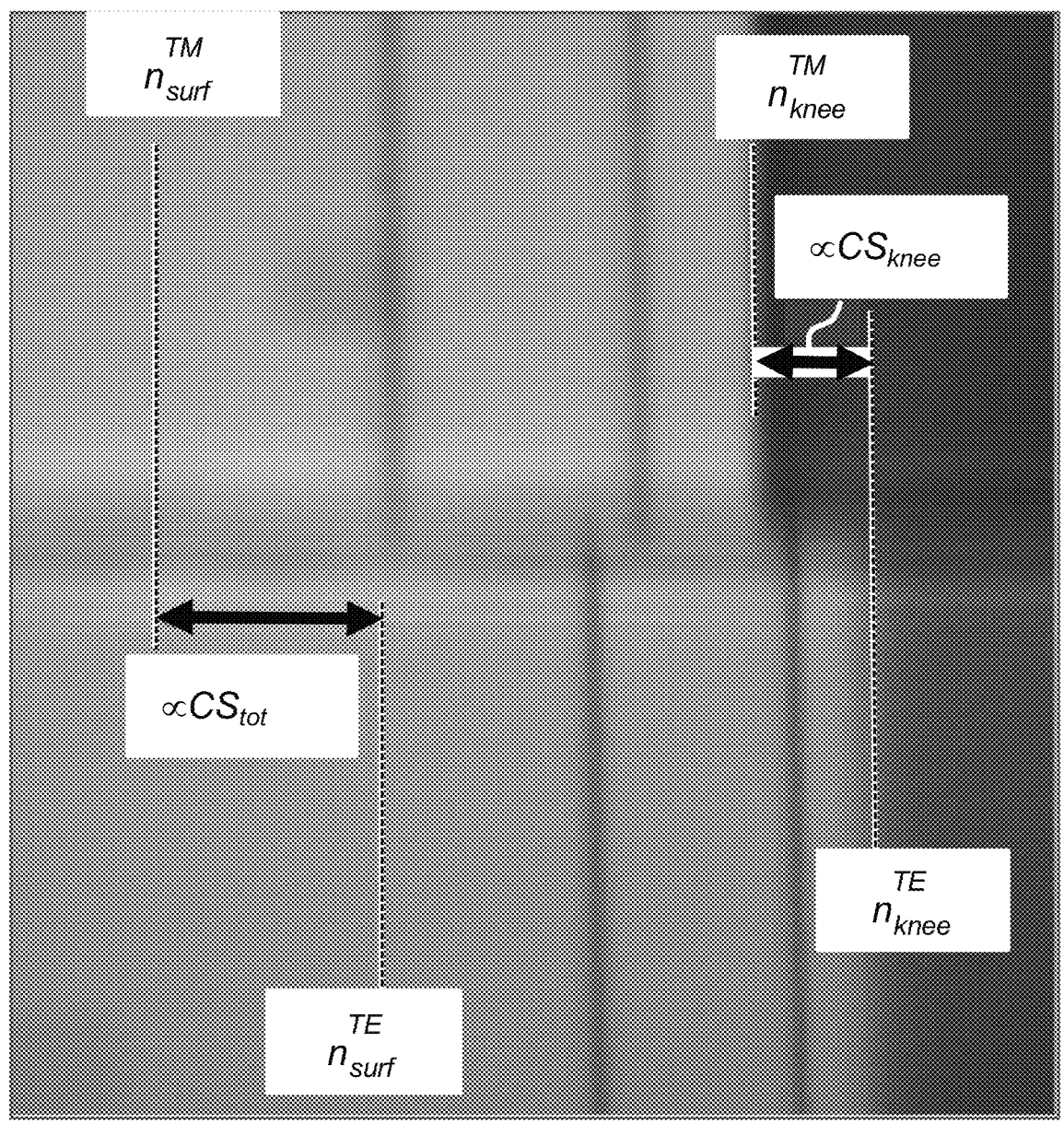
FIGS. 3A and 3B are a photograph and a schematic diagram, respectively, of a mode spectrum based on a measured mode spectrum of a Li-containing glass formed by an ion-exchange process using a mixture of $NaNO_3$ and $KNO_3$, with the mode spectrum including a TM spectrum (top) and a TE spectrum (bottom), and also showing select profile measurement parameters pertinent to carrying out the methods disclosed herein.
Figure 3B:
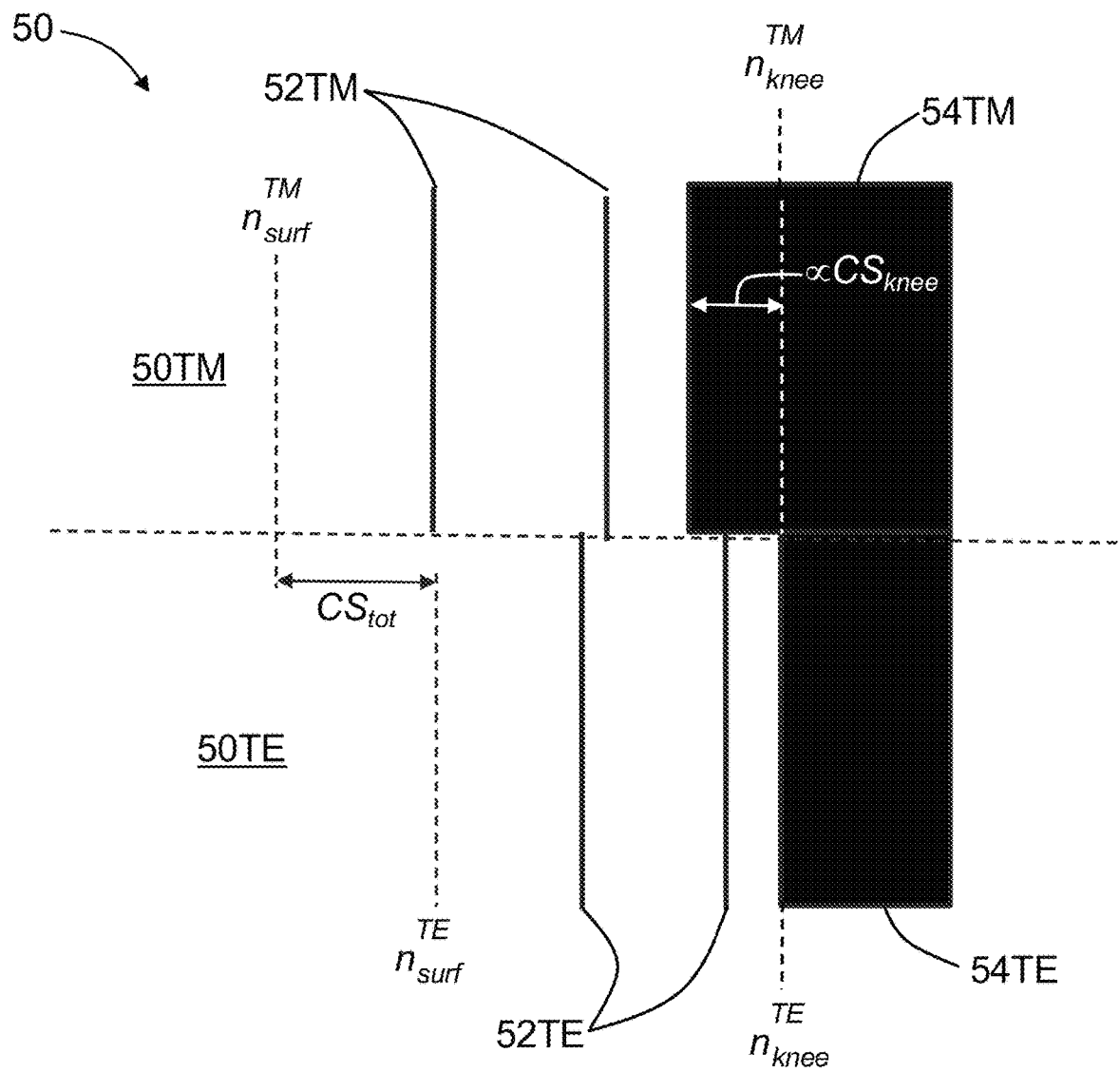

FIG. 3A is photograph of example measured mode spectrum 50 and FIG. 3B is a schematic diagram of the measured mode spectrum of FIG. 3A, which is for Li-containing glass formed by an ion-exchange process using a mixture of $NaNO_3$ and $KNO_3$. The mode spectrum 50 includes TM and TE spectra 50TM and 50TE (upper and lower portions, respectively) with respective mode lines 52TM and 52TE that represent higher-order modes. The lower-order modes lines in the TM and TE mode spectra 50TM and 50TE are tightly bunched together and are shown as respective solid black regions denoted as 54TM and 54TE. The glass type for the measured sample was 196HLS with a fictive temperature of 638° C. The glass sample was subjected to a Li+⇔K+, Na+ ion-exchange process by placing the glass sample in a bath having 60 wt % $KNO_3$ and 40 wt % $NaNO_3$ at 390° C. for 3 hours.

As is known in the art, the fringes or mode lines 52TM and 52TE in the mode spectrum can be used to calculate surface compression or "compressive stress" CS and depth of layer DOL associated with an ion-exchange layer that forms an optical waveguide. In the present example, the mode spectrum 50 on which FIGS. 3A and 3B are based was obtained using a commercially available prism-coupling system, namely the FSM6000L surface stress meter ("FSM system"), available from Luceo Co., Ltd. of Tokyo, Japan. Example prism-coupling systems suitable for use for carrying out the methods disclosed herein are also described in U.S. Patent Applications No. 2014/0368808 and 2015/0066393, which are incorporated by reference herein.

The measured values of CS and DOL were 575 MPa and 4.5 microns, respectively. These are the parameters of the K+ enriched layer or spike region R1 adjacent sample surface 22 (see FIG. 2). The vertical dashed lines on the left hand side of the spectrum of FIG. 3A show positions in the spectrum that correspond to the surface index, one for TM, and one for TE. The difference in these positions, as indicated by the black arrows, is proportional to the surface stress or compressive stress CS. One of the black arrows in FIG. 3A is denoted $CS_{tot}$, while the other is denoted $CS_{knee}$ or $CS_k$ or and are discussed below. These values are used in the calculation of DOL.

In the mode spectrum 50 for a chemically strengthened Li-containing glass having undergone a (Li+⇔K+, Na+) ion exchange, the relative positions of the TM and TE mode spectra 50TM and 50TE are shifted. This shift can be measured by the relative positions of the last (i.e., left-most) fringes 52TM and 52TE, which correspond to the highest-order guided modes. As noted above, this shift is denoted $CS_{tot}$ in FIGS. 3A and 3B and is proportional to the compressive stress CS at the depth at which the K+ concentration in spike region R1 decreases approximately to the constant-level concentration originally in the substrate (e.g., the spatially constant concentration in the glass matrix that makes up substrate body 21).

The effective index of the transition corresponds to the effective index that occurs at the depth of a characteristic "knee" or transition KN in the stress profile, and is denoted in FIGS. 3A and 3B for the TM and TE mode spectra 50TM and 50TE, respectively. The shift of the transition between the TE and TM spectra is proportional to the compressive stress at the depth of the knee KN and denoted $CS_{knee}$ in FIGS. 3A and 3B.

The direct measurement of the knee stress $CS_{knee}$ from the birefringence of the critical-angle intensity transition of the TE and TM mode lines 52TE and 52TM presents some problems. One problem is due to shifting of the apparent position of the transition when a leaky mode or a guided mode has effective index very close to the index corresponding to the critical angle. For example, the broader dark fringe can occur approximately at the same location as the critical-angle transition in the upper half of the combined spectra of FIGS. 3A and 3B.

Figure 6A:
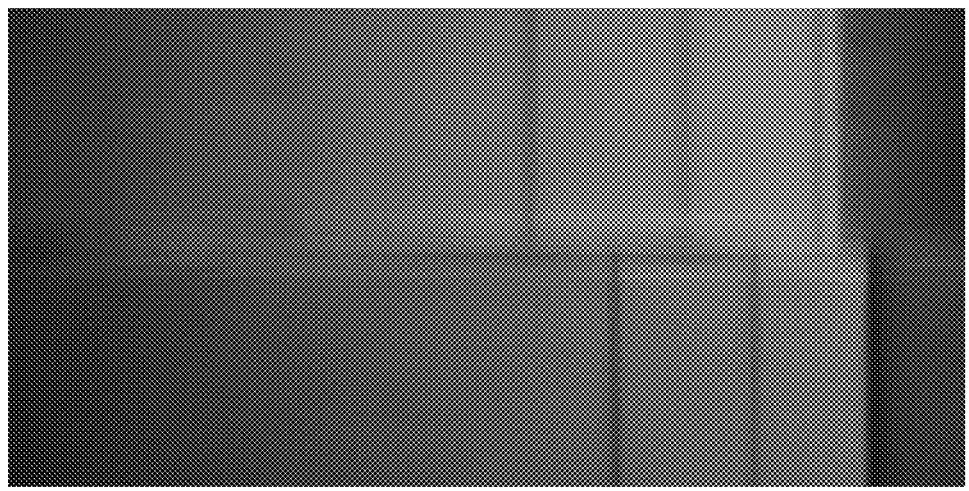
FIGS. 6A and 6B are a photograph and a schematic diagram, respectively, of a mode spectrum based on a measured mode spectrum and showing the TE and TM mode spectra for an example chemically strengthened Li-containing glass sample.
Figure 6B:
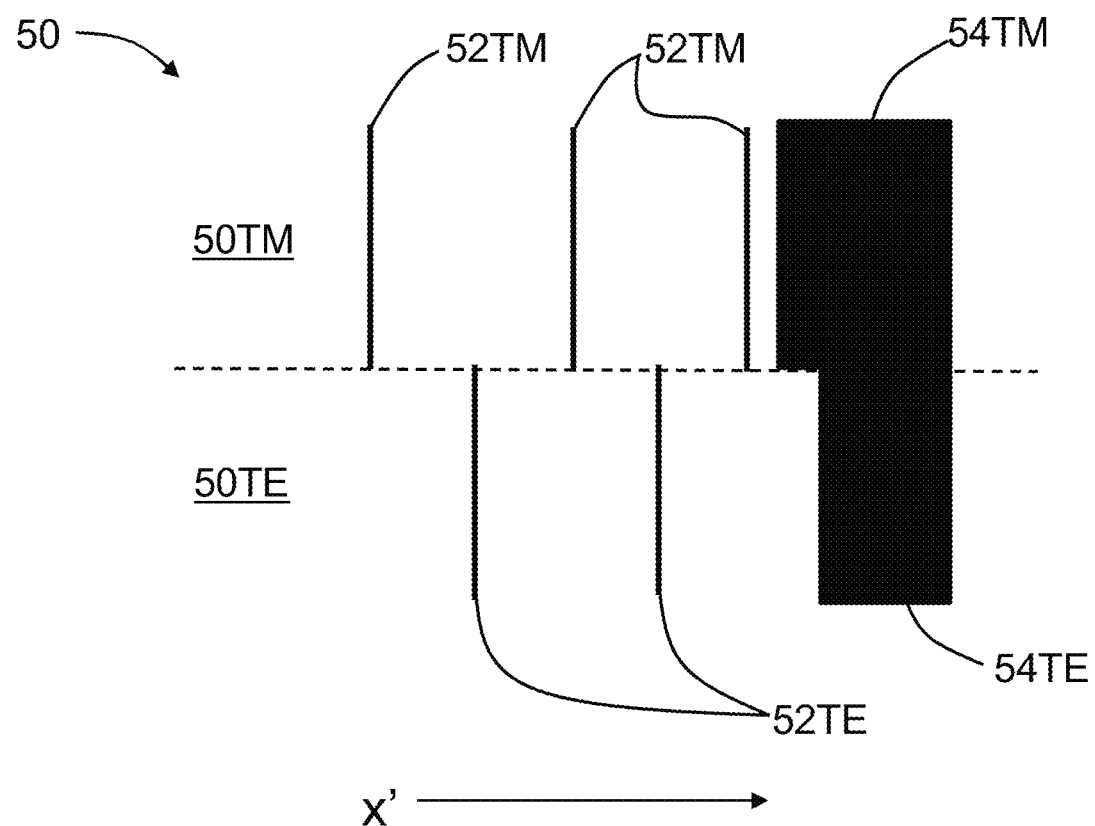
Figure 6C:
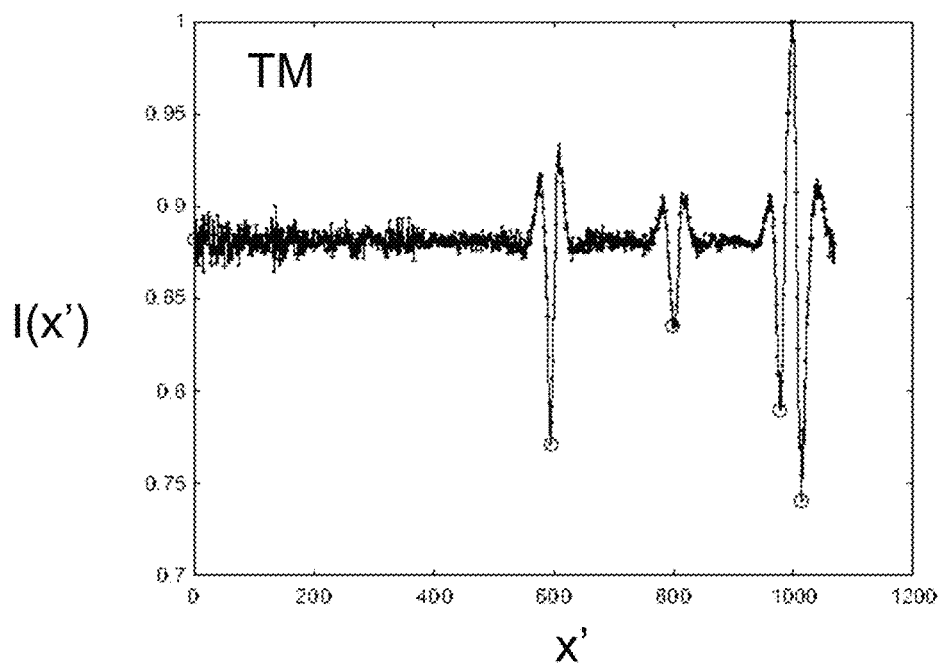
FIGS. 6C and 6D are plots of the intensity I versus distance x' along the mode spectrum for the mode lines or fringes of TE and TM mode spectra, respectively, of FIG. 6A.
Figure 6D:
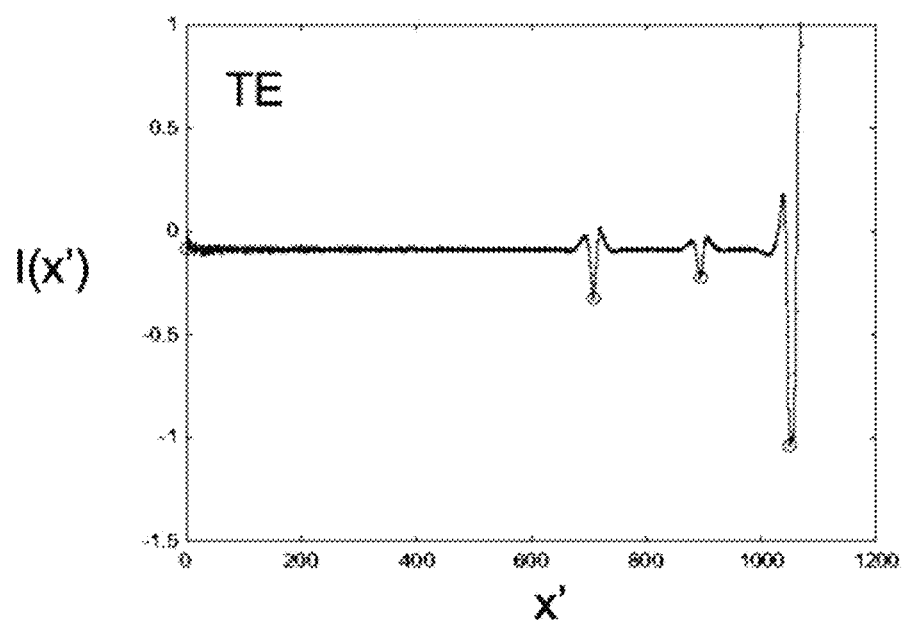

FIGS. 6A and 6B are a photograph and a schematic diagram, respectively, of an example measured mode spectrum and showing the TE and TM mode spectra for an example chemically strengthened Li-containing glass sample. FIGS. 6C and 6D are plots of the intensity I versus distance x' (I(x')) along the mode spectrum for the mode lines or fringes 52TE and 52TM of TE and TM mode spectra, respectively, of FIG. 6A. The intensity profiles show the detection of the position x' of the pixels corresponding to the positions of the fringe and the transition between the spike region and the continuum (last peak) for the TM and TE modes. The position in pixels is essentially a measurement of the index of refraction of the modes and the transition region.

Avoiding the aforementioned shift-induced error requires that both the upper and lower spectra (i.e., the TM and TE spectra 50TM and 50TE) the have a fractional part of the mode number between about 0.2 and 0.6, which is quite restrictive. In addition, even when this condition is satisfied, the measurement of the critical angle for the TE spectrum is not very precise due to a relatively blurry TE intensity transition. Note for example how the critical-angle transition in the bottom half of FIGS. 3A and 3B is relatively broad, rather than sharp; in contrast, the critical-angle TM transition shown in FIG. 6A is narrow (sharp) even though there is no dark fringe close to it.

The methods disclosed herein utilize measurements of the fringe spectrum provided by the potassium penetration resulting from ion exchange, along with the position of the intensity transition in the TM spectrum (e.g., transition from total internal reflection (TIR) to partial reflection) relative to the positions of the TM fringes. These measurements can be combined and used for effective quality control of a family of stress profiles that help enable superior resistance to fracture during face drops. The profiles of this family are similar in shape to a power-law profile with a spike.

The spike SP is a near-surface region that has a small thickness when compared to the substrate thickness. For example, the spike may be 10 μm deep, while the substrate may be 800 μm thick. The spike may have a shape similar to erfc-shape, but may also be similar to a linear depth distribution, Gaussian depth distribution, or another distribution. The main features of the spike are that it is a relatively shallow distribution and provides substantial increase of surface compression over the level of compression at the bottom (deepest end) of the spike, which ends at knee KN.

Figure 4:
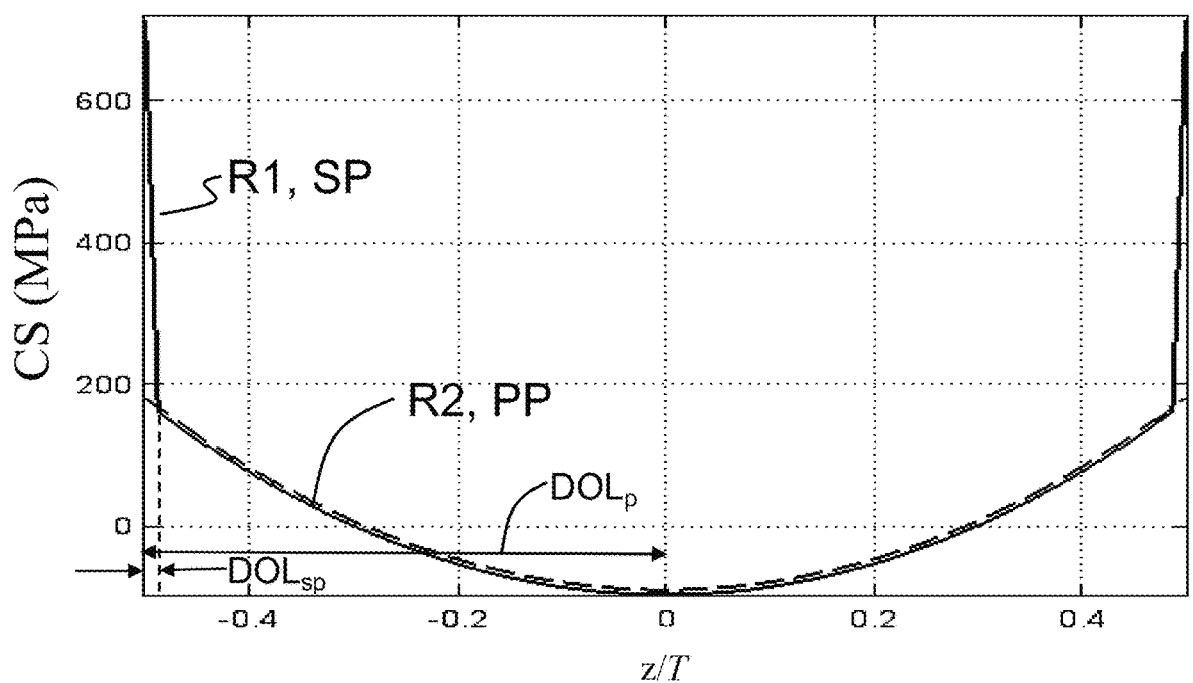
FIG. 4 is a plot of the compressive stress CS (MPa) versus a normalized position coordinate z/L, showing the model stress profile (solid line) for a sample chemically strengthened Li-containing glass that has undergone a K+ and Na+ ion exchange, wherein the dashed line curve represents the model profile for Na+ diffusion only, noting that the model profile has ion exchange taking place at two surfaces that respectively reside at z/T=−0.5 and +0.5.

FIG. 4 shows a model stress profile having a power-law portion PP in region R2 and surface spike SP in region R1, as shown in FIG. 2. For the purposes of the present disclosure, the assumed convention is that compressive stress is positive and tensile stress is negative. The model profile of FIG. 4 has a linear spike SP added on top of a deep quadratic profile for power-law portion PP.

Another feature of the spike SP in FIG. 4 is also recognized from FIG. 2, namely that the typical slope of the stress distribution in the spike SP is significantly higher than the typical slope in the power-law portion PP of the profile. In an example, the power-law portion PP is assumed to be well-described by a power-function of the distance from the center-plane of the glass substrate, with a power exponent in the range between about 1.5 and about 4.5. In an example, this auxiliary power-law portion PP can be assumed near-parabolic, and approximated as parabolic for the purposes of quality-control measurements.

In one embodiment of the method, the $CS_{SP}$ and $DOL_{SP}$ of the spike SP are measured using a traditional FSM measurement. For increased precision of the DOL measurement, it may be preferred that the $DOL_{SP}$ of the spike be measured using the TM spectrum only, as the critical-angle transition in the example Li-containing glasses exchanged in mixtures of Na and K is substantially sharper and less prone to measurement errors. Note that in the present disclosure the denominations DOL and $DOL_{SP}$ are used interchangeably to refer to the same quantity, namely, the depth of layer of the K-enriched near-surface spike layer having high compressive stress $CS_{SP}$.

A center tension CT contribution of the spike is calculated using the equation $$CT_{sp} = \frac{CS_{SP} \times DOL_{sp}}{T - DOL_{sp}}$$

where T is the sample thickness (see FIG. 1). The contribution to the center tension CT of the Na profile can be associated with the measured knee stress $\sigma_{knee}$. A crude estimate can be found by assuming that the surface stress of the auxiliary profile used to describe the stress produced by the Na distribution is approximately the same as the stress at the knee. Thus, we have:

$$CT_p \approx \frac{|\sigma_{knee}|}{p}$$

where $\sigma_{knee}$ is the stress at the knee of the profile, e.g., at the bottom of the spike and is given by:

$$\sigma_{knee} = \frac{(n_{crit}^{TE} - n_{crit}^{TM})}{SOC}$$

where $n_{crit}^{TE}$ and $n_{crit}^{TM}$, are the effective indices of the critical-angle intensity transitions as illustrated on FIGS. 3A and 3B. The parameter SOC is the stress-optic coefficient. The numerator in the above expression can be defines as the birefringence BR, in which case the equation reads:

$\sigma_{knee} = CS_{knee} = BR/SOC$.

This equation can also be written more generally as $\sigma_{knee} = CS_{knee} = (CFD)(BR)/SOC$ where CFD is calibration factor between 0.5 and 1.5 that accounts for systematic offsets between the recovered critical-angle values having to do with fundamentally different slopes of the TM and TE intensity transitions, different shape of the TM and TE index profiles in the vicinity of the knee, and specifics of the method by which the location of the intensity transition is identified. As noted above, the parameters or $\sigma_{knee}$, $CS_{knee}$, $CS_k$ and $CS_K$ all refer to the same quantity, namely, the knee stress.

As illustrated by the dashed line curve in FIG. 4, the assumed power-law or power-law profile for power-law portion PP may be taken as an auxiliary profile that does not include the spike, but extends the power-law or parabolic shape all the way to the surfaces of the sample. This auxiliary profile is force-balanced, having its own compressive tension CT, and is hence shifted vertically from the power-law portion of the model spiked power-law profile.

Auxiliary Power-Law Profile Relationships

A detailed description of the relationships that hold for the auxiliary power-law profile is now provided, as well as the associated method of using them to calculate the parameters of the model spiked profile for the purposes of quality control.

The auxiliary power-law profile provides the stress as a function of distance z from the center.

$$\sigma_p(z) = CT_p - \sigma_0 \left(\frac{z}{0.5T}\right)^p$$

$$CT_p = \frac{CS_p}{p}$$

$$DOC_p = 0.5T\left(1 - \frac{1}{(1+p)^{\frac{1}{p}}}\right)$$

The spiked profile has a somewhat smaller depth of compression DOC given by the expressions $$DOC = 0.5T\left(1 - \left(\frac{CT_{tot}}{(1+p)CT_p}\right)^{\frac{1}{p}}\right) \equiv 0.5T\left(1 - \left(\frac{1}{1+p}\left(1 + \frac{CT_{sp}}{CT_p}\right)\right)^{\frac{1}{p}}\right)$$

The depth of compression DOC of the spiked profile is smaller than that of the auxiliary power profile by approximately:

$$\Delta DOC \approx -\frac{0.5t}{(1+p)^{\frac{1}{p}}} \times \frac{CT_{sp}}{pCT_p}$$

The change in the depth of compression DOC caused by the spike in the profile can be normalized to the compressive tension CT of the auxiliary power profile as follows:

$$\frac{\Delta DOC}{DOC^{aux}} \approx \frac{\frac{0.5T}{(1+p)^{\frac{1}{p}}} \times \frac{CT_{sp}}{pCT_p}}{0.5T\left(1 - \frac{1}{(1+p)^{\frac{1}{p}}}\right)} = -\frac{CT_{sp}}{p((1+p)^{\frac{1}{p}} - 1)CT_p}$$

In the specific example of a parabolic auxiliary profile, the following relationships hold:
The auxiliary profile has a compression depth $DOC_{par}$ given by:

$$DOC_{par} = 0.5T\left(1 - \frac{1}{\sqrt{3}}\right) \approx 0.2113\ T$$

The total center tension $CT_{tot}$ of the profile equals the sum of spike center tension $CT_{sp}$ and the parabolic portion center tension $CT_p$:

$CT_{tot} = CT_p + CT_{sp}$

The depth of compression DOC of the spiked power-law profile can be calculated by using the expression:

$$DOC = 0.5T\left(1 - \sqrt{\frac{CT_{tot}}{3CT_{par}}}\right) = 0.5T\left(1 - \sqrt{\frac{1}{3}\left(1 + \frac{CT_{sp}}{CT_{par}}\right)}\right) \approx$$

$$DOC_{par}\left(1 - \frac{CT_{sp}}{2CT_{par}(\sqrt{3}-1)}\right) \approx DOC_{par} - \frac{0.5T}{\sqrt{3}}\frac{CT_{sp}}{2CT_{par}}$$

The approximate expressions at the end of the above equation are valid when the CT contribution of the spike is significantly smaller than the CT contribution of the auxiliary profile (i.e., the parabolic portion PP).

Example Method Based on Approximation

An example method of quality control utilizes an approximation approach that includes a measurement of the mode spectrum due to the spike. The method then includes estimating a contribution of the spike to the center tension CT by estimating a compression at the knee KN of the profile and subtracting that knee compression from the surface compression in the calculation of the spike contribution to the center tension. The method then includes estimating a contribution to the center tension CT due to the deep power-law profile portion PP excluding the spike, also taking advantage of the estimated knee stress. The method then includes finding the total center tension $CT_{tot}$ as a sum of the contributions of the auxiliary deep power-law profile and of the spike, i.e., $CT_{tot}=CT_{sp}+CT_p$. In general, the CT contribution of the deep portion may be denominated $CT_{deep}$, which can be interchangeably used with $CT_p$ when the deep portion is represented as having a power-law shape.

In addition, the method can include estimating the compression depth DOC of the profile by using an exact formula for the model profile, or an approximate formula that gives the DOC as the DOC of an auxiliary power-law profile less a small DOC reduction due to the spike, i.e., $DOC=DOC_p+\Delta DOC_{sp}$, (in the mathematical formula a negative $\Delta DOC_{sp}$ is added to $DOC_p$). Note also that $\Delta DOC_{sp}$ is sometimes labeled simply as $\Delta DOC$ in the present disclosure, as only the shift in DOC that is due to the spike is considered in this disclosure.

In one example of the method, the DOL of the spike SP is used to verify that the power-law portion PP of the profile (see FIG. 4) is in a regime that is well represented by the power-law profile shape. In particular, as the DOL of the spike increases, the penetration of Na increases approximately in proportion to the DOL of the spike. Thus, for a glass substrate where simultaneous in-diffusion of K and Na is used, a minimum spike $DOL_{SP}$ can be set for any particular glass thickness, above which the deep portion of the profile can be considered parabolic. In another example, an upper limit of the $DOL_{SP}$ may also be imposed, to exclude physical profiles that start to deviate substantially from the assumed power-law model.

More Precise Method

The above-described method is based on approximation and is thus a somewhat more simplified version of a more precise method. The simplification incurs only a minor error when the CT contribution of the spike is much smaller than the CT contribution of the auxiliary power-law profile. The CT contribution of the spike shifts the deep power-law portion PP vertically by the amount $CT_{sp}$ relative to the auxiliary power-law profile. As a result, the compression at the knee of the model spiked profile is actually smaller than the compression of the auxiliary profile at the knee depth by the amount $CT_{sp}$.

Furthermore, there is a minor change in compression of the auxiliary power-law profile between the surface and the depth of the knee, and, for a force-balanced power-law profile the CT is actually equal to $$\frac{CS_p}{p}.$$

The following represents an example of a more precise method for determining the parameters of the model spiked power-law profile from the mode spectrum as obtained from prism-coupling measurements of a chemically strengthened glass sample:

a) Calculate preliminary $$CT_{sp}^{(0)} = \frac{(CS_{tot} - CS_{knee}) \times DOL_{sp}}{T - DOL_{sp}}$$

b) Calculate preliminary surface compression of the auxiliary profile $$CS_p^{(0)} = p\frac{CS_{knee} + CT_{sp}^{(0)}}{(p+1)\left[1 - \frac{2DOL_{sp}}{T}\right]^p - 1}$$

c) (Optional alternative to steps 4, 5, and 6) Calculate preliminary $$CT_p^{(0)} = \frac{CS_p^{(0)}}{p} = \frac{CS_{knee} + CT_{sp}^{(0)}}{(p+1)\left[1 - \frac{2DOL_{sp}}{T}\right]^p - 1} \text{ and } CT_{tot}^{(0)} = CT_p^{(0)} + CT_{sp}^{(0)}$$

d) Calculate more precise $$CT_{sp}^{(1)} = \frac{(CS_{tot} - CS_p^{(0)}) \times DOL_{sp}}{T - DOL_{sp}}$$

e) Calculate more precise $$CS_p^{(1)} = p\frac{CS_{knee} + CT_{sp}^{(1)}}{(p+1)\left[1 - \frac{2DOL_{sp}}{T}\right]^p - 1},$$

$$\text{and } CT_p^{(1)} = \frac{CS_p^{(1)}}{p} = \frac{CS_{knee} + CT_{sp}^{(1)}}{(p+1)\left[1 - \frac{2DOL_{sp}}{T}\right]^p - 1}$$

f) Calculate more precise $CT_{tot}^{(1)}=CT_p^{(1)}+CT_{sp}^{(1)}$ g) (Optional; usually unnecessary)—can continue iteration, finding more and more precise values for $CT_{sp}$ and $CS_{par}$ until desired level of convergence or precision. More than one iteration would rarely be needed. More than one iteration may be useful in relatively thin substrates in which the depth of the spike may represent more than about 3% of the substrate thickness.

h) (Optional) Determine depth of compression of the profile, for example using one of the forms of the equation:

$$DOC = 0.5T\left(1 - \left(\frac{CT_{tot}}{(1+p)CT_p}\right)^{\frac{1}{p}}\right) \equiv 0.5T\left(1 - \left(\frac{1}{1+p}\left(1 + \frac{CT_{sp}}{CT_p}\right)\right)^{\frac{1}{p}}\right)$$

The above-described method allows for the application of the generic auxiliary power-law profile for the QC of a spiked double-ion-exchanged profile having a stress distribution reasonably well described by a spiked power-law profile model. The method avoids a direct measurement of the knee stress. Instead of directly measuring $n_{crit}^{TE}$ to evaluate the knee stress from the earlier described equation, $$\sigma_{knee} = \frac{(n_{crit}^{TE} - n_{crit}^{TM})}{SOC},$$

the knee stress is found by observing that it occurs at a depth equal to the penetration of the spiking ion, e.g., at a depth of spike $DOL_{sp}$.

$$CS_{knee} \equiv \sigma_{knee} = \sigma(depth = DOL_{sp}).$$

The above strict definition of the knee stress is most easily understood for the case where the profile has an abrupt change in slope at the location of the knee. In practice, most profiles change slope gradually, although fast, in the vicinity of depth=$DOL_{sp}$, and σknee occurs approximately at depth=$DOL_{sp}$ as measured from the mode spectrum. Hence, in the calculation of σknee often a calibration factor of magnitude comparable to 1 is used, in part to account for differences between the continuous distribution of stress and the abrupt change in stress slope in a simple explicit description of a model having a steep linear truncated stress spike connected to a deep region of slowly varying stress.

The surface stress and its slope are obtained from the prism-coupling measurements of the effective indices of the TM and TE modes confined in the depth region of the spike by a measurement of the CS, the stress slope $s_\sigma$ and DOL of the spike.

The surface stress and the slope of a linear spike can be found using the following analysis: Using the WKB approximation the turning points $x_1$ and $x_2$ of the two lowest-order modes in an optical waveguide can be found using the relations $$x_1 = \frac{9}{16}\frac{\lambda}{\sqrt{n_0^2 - n_1^2}}$$

$$x_2 = \frac{21}{16}\frac{\lambda}{\sqrt{n_0^2 - n_2^2}}$$

where $n_0$ is the surface index of the profile having linearly decreasing with depth dielectric susceptibility, $n_1$ is the index of the lowest-order mode, $n_2$ is the effective index of the second-lowest-order mode, and λ is the optical wavelength. The surface index of the linear profile is found from the same first two modes by the relation:

$$n_0^2 = n_{surf}^2 \approx n_1^2 + 1.317014(n_1^2 - n_2^2)$$

For profiles having $n_1 - n_2 \ll n_1$, an even simpler relation can be used:

$$n_0 \equiv n_{surf} \approx n_1 + 1.3(n_1 - n_2)$$

The index slope of each of the TM and TE index profiles associated with the stress profile of the spike is then given by:

$$s_n = \frac{n_1 - n_2}{x_1 - x_2}.$$

The above relations for the surface index and the index slope of the linear profile can be applied for both the TM and TE mode spectra, to obtain the TM and TE surface indices $n_{surf}^{TM}$ and $n_{surf}^{TE}$ and the TM and TE profile index slopes $s_n^{TM}$ and $s_n^{TE}$. From these, the surface stress CS, and the stress slope $s_\sigma$ can be obtained:

$$CS = \frac{n_{surf}^{TE} - n_{surf}^{TM}}{SOC}$$

$$s_\sigma = \frac{s_n^{TE} - s_n^{TM}}{SOC}$$

where as noted above, SOC stands for stress-optic coefficient. Note that when more than two guided modes are supported in either the TM or TE polarization, or both, then the precision of the slope measurement can be improved by taking advantage of the measured effective indices of more than two modes per polarization, by using a linear regression to associate the measured effective indices of multiple modes with a single index slope for each polarization.

There is now one step left to obtain the knee stress, namely a measurement of the spike depth $OL_{sp}$, which is obtained by analysis of the TM spectrum. The index space between the highest-order guided mode and the index corresponding to the TM critical angle is assigned a fraction of a mode based on what fraction it represents of the spacing of the previous two modes, and, if desired for higher precision, on how many guided modes are guided. This type of DOL calculation is routinely done by the FSM-6000 instrument.

Finally, the depth of the spike is given by the formula:

$$DOL_{sp} = \frac{3}{4}\lambda\frac{N - \frac{1}{4}}{\sqrt{2n_{av}(n_{surf} - n_{crit})}}$$

where N is the number of guided TM modes, including the fraction of a mode assigned to the space between the last guided mode and the critical index $n_{crit}$ of the intensity transition, A is the measurement wavelength, and $n_{crit}$ is the effective index corresponding to the critical angle in the TM spectrum, indicated as $n_{knee}^{TM}$ in FIGS. 3A and 3B.

With $DOL_{sp}$ measured with good precision from the TM coupling spectrum, the knee stress $CS_{knee}$ at the bottom of the spike is found using the relationship:

$$CS_{knee} \equiv \sigma_{knee} \equiv \sigma_{sp}(x = DOL_{sp}) = CS + s_\sigma \times DOL_{sp}$$

Accounting for systematic differences between real profiles in the vicinity of the knee point, and the assumed model for the spike shape, the knee stress can be found by the following more general relationship:

$$CS_{knee} \equiv \sigma_{knee} \equiv \sigma_{sp}(x = DOL_{sp}) = CS + KCF \times s_\sigma \times DOL_{sp}$$

where the knee calibration factor KCF is usually between 0.2 and 2, and serves to account for the difference in shape between a real spike distribution and the assumed model of the spike shape, as well as the particular way that the $DOL_{sp}$ is calculated from the mode spectrum. For example, a commonly used equation for the surface index is $$n_0 \equiv n_{surf} \approx n_1 + 0.9(n_1 - n_2).$$

which uses a factor of 0.9 instead of the factor 1.317 which is accurate for linear spikes. When the formula for surface index with a factor of 0.9 is used, the resulting calculated DOL appears higher than the purely linear-spike DOL.

This improved method of measurement of the knee stress by use of a precise measurement of $DOL_{sp}$, when used in the approximate algorithm or in the more precise in the iterative algorithm for extraction of the parameters of the spiked deep profile described above for the general power-law auxiliary profile (or in the previous disclosure for the quadratic auxiliary profile), provides a quality-control method with improved precision of the estimate of CT for frangibility control. The knee stress is by itself an important parameter of glass strength and the precision improvement of that parameter is also of value. The improved method also increases the breadth of the sweet spot for measurement typically by a factor of two or even more.

In another embodiment involving indirect measurement of the knee stress, the method makes use of a strong correlation between the knee stress and the birefringence of the last guided mode of the spike. When the spike CS and DOL are kept in very narrow respective ranges, then a strong correlation forms between the sought after knee stress and the difference in the effective index between the last guided TM mode and the last guided TE mode of the spike.

The method exploits the birefringence of the last guided mode of the spectrum acquired by the prism coupler for quality control (QC) measurements. Here we will use formulas for a generic power profile with exponent 'n'. For a power-law profile n=2, for cubic n=3 but also fractional profiles like n=2.37 is possible for making the equations generic. In the present disclosure, when n refers to a power of the profile, it has the same meaning as p which is also used to denominate the power of the auxiliary deep profile.

Figure 5:
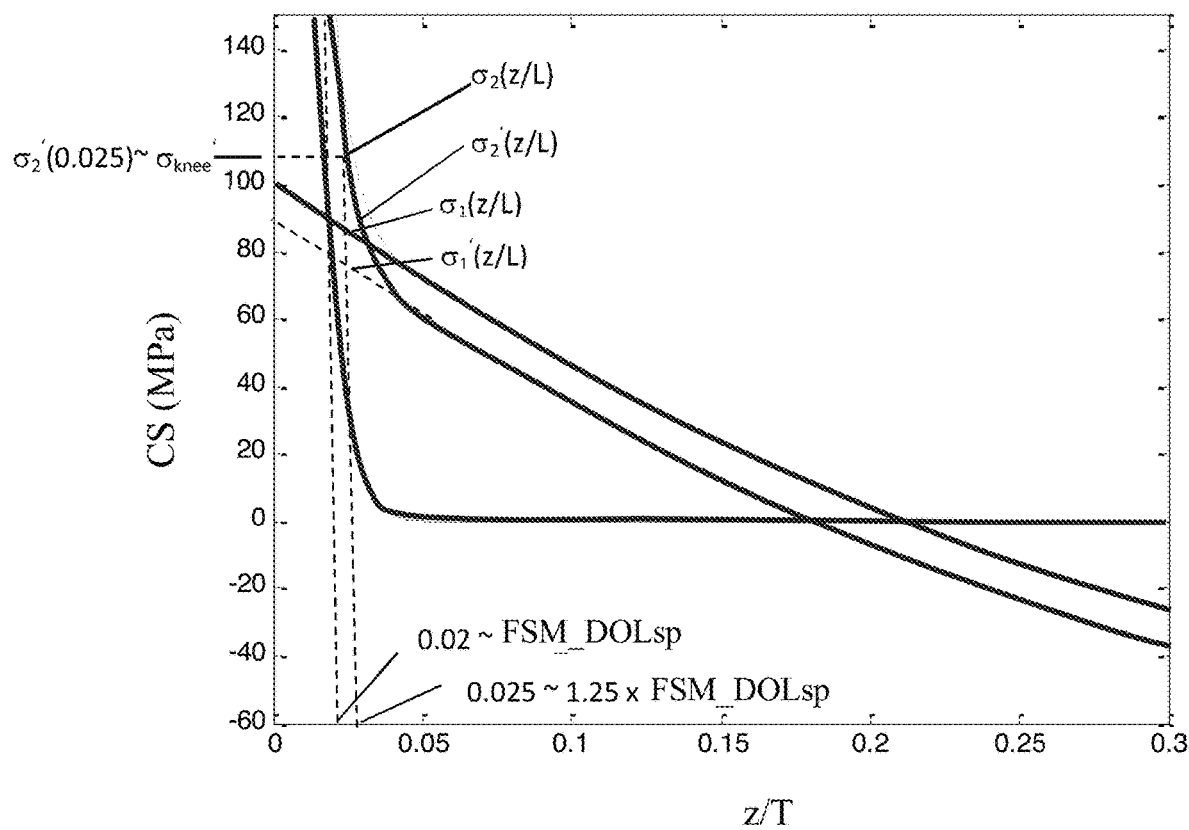
FIG. 5 is a plot of the stress (MPa) versus a normalized position coordinate z/L showing separate plots for the spike portion, the long diffused parabolic portion and the spike plus parabolic portion of the stress profile.

Using the power (parabolic for n=2 in this case) auxiliary profile, illustrated with the help of FIG. 5, the following representation is used for the force-balanced profile:

$$\sigma\left(\frac{z}{L}\right) = CS\left[\left(1 + \frac{1}{n}\right)\left|2\frac{z}{L} - 1\right|^n - \frac{1}{n}\right] \quad (1)$$

where L is the thickness. The depth of layer $DOL_{deep}$ of the deep part of this power profile with exponent 'n' is given by $$\frac{DOC_{deep}}{L} = 0.5\left(1 - \frac{1}{(1+n)^{\frac{1}{n}}}\right) \quad (2)$$

The FSM measures FSM_DOL of the spike as approximately the diffusion depth given by $2\sqrt{D\tau}$ where D is the diffusion coefficient and $\tau$ is the time of diffusion.

For a spike with the shape of erfc-function, it is empirically found that the knee stress can be assumed to occur at a depth of $\sim K_1 \times FSM\_DOL = 1.25 \times FSM\_DOL$, such that most of the stress-area of the spike to be included in the CT calculation.

One can get an approximate equation for the $\Delta CT_{spike}$ due to the spike contribution. Here, $K_1$ is an empirical factor set at 1.25 for this particular case. The factor $K_1$ serves to compensate for nonzero residual stress contributed by the tail of the spike at depth=FSM_DOL by adjusting the point at which the knee stress is estimated.

$$\Delta CT_{spike} = \frac{(\sigma_2'(0) - \sigma_2'(K_1 \times FSM\_DOL)) \times K_1 \times FSM\_DOL}{T - K_1 \times FSM\_DOL} \quad (3)$$

The point $\sigma_2'(K_1 \times FSM\_DOL) = \sigma_2'(1.25 \times FSM\_DOL)$ is very close to the CS between the transition between guided modes and continuum in the spiked lithium glass samples. This point is called the $CS_{knee}$ as shown in FIGS. 3A and 3B as a reasonable approximation. It is also reasonable to approximate the stress and the offset due to the contribution of the $CT_{spike}$ deeper inside the glass.

Since the power-law profile will be slow varying compared to the spike, it can be assumed that the stress at $\sim(K_2) \times FSM\_DOL \cdot (1-3) \times FSM\_DOL$ in the parabolic region would not feel the presence of the spike.

This allows the following approximations to be employed:

$$\sigma_1\left(\frac{z}{L}\right) \cong \sigma_1'\left(\frac{z}{L}\right) + \Delta CT_{spike} \quad (4)$$

and, $$\sigma_1\left(\frac{K_2 \times FSM\_DOL}{L}\right) \cong \sigma_1'\left(\frac{K_2 \times FSM\_DOL}{L}\right) + \Delta CT_{spike} \quad (5)$$

where using the parabolic equation in (1), it is found that:

$$\sigma_1\left(\frac{K_2 \times FSM\_DOL}{L}\right) = \sigma_1(0)\left[\left(1 + \frac{1}{n}\right)\left(K_2 \times \frac{2 \times FSM\_DOL}{L} - 1\right)^n - \frac{1}{n}\right] \quad (6)$$

$$\cong \sigma_1'\left(\frac{K_2 \times FSM\_DOL}{L}\right) + \Delta CT_{spike}$$

and $$\sigma_1(0) \cong \frac{\sigma_1'\left(\frac{K_2 \times FSM\_DOL}{L}\right) + \Delta CT_{spike}}{\left[\left(1 + \frac{1}{n}\right)\left(K_2 \times \frac{2 \times FSM\_DOL}{L} - 1\right)^n - \frac{1}{n}\right]} \quad (7)$$

The factor $K_2$ accounts for nonzero spike stress distribution beyond the depth $DOL_{sp}$ calculated from the mode spectrum.

It can be demonstrated that if one uses a factor 2 instead of 3 the results are almost the same, in some cases varying just 1%-3% of $\sigma_1(0)$. Therefore, if one can find the approximated value of $$\sigma_1'\left(\frac{3 \times FSM\_DOL}{L}\right) \text{ or } \sigma_1'\left(\frac{1 \times FSM\_DOL}{L}\right)$$

in the FSM, formula (6) can be used to compute the original stress of the first stress parabola within this range of error.

In practice one can measure approximately $$\sim\sigma_1'\left(\frac{3 \times FSM\_DOL}{L}\right) \text{ to } \sim\sigma_1'\left(\frac{1 \times FSM\_DOL}{L}\right)$$

by looking at the stress generated at the transition between guided modes and continuum in the spike on Li-glass samples.

This point, where approximately $$\sim\sigma_1'\left(\frac{3 \times FSM\_DOL}{L}\right) \text{ to } \sim\sigma_1'\left(\frac{1 \times FSM\_DOL}{L}\right),$$

can be used as the point $CS_{knee}$ as shown in FIGS. 3A and 3B as a reasonable approximation, that can be measured by computing the distance between the mode lines in TM and TE polarization and their refractive index. In light of the stress optical coefficient SOC of the material the division of the index difference at this point per the SOC would lead to the $CS_{knee}$ stress values.

This is in addition to the FSM_DOL and the CS~$\sigma_2'(0)$ given by the FSM for the spike. Therefore $CT_{deep}=\sigma_1(0)/n$, where for a parabolic deep profile n=2, and $\Delta CT_{spike}$ is given in (3) as (repeated for convenience)

$$\Delta CT_{spike} = \frac{(\sigma_2'(0) - \sigma_2'(K_1 \times FSM\_DOL)) \times K_1 \times FSM\_DOL}{T - K_1 \times FSM\_DOL} \quad (3)$$

From there one can (repeating the previous equations) then compute the total center tension equals the sum of the contributions of the spike and of the parabolic portion:

$$CT_{tot} = CT_{deep} + \Delta CT_{spike} \quad (7)$$

If desired the depth of compression of the spiked power-law profile can be calculated/estimated by using the expression:

$$DOL_{total} = DOL_{deep} - \frac{DOL_{deep}}{n \cdot CT} \Delta CT_{spike}. \quad (8)$$

These equations assume that the deep part of the profile is a generic power profile (parabolic for n=2) in nature and has an added spike near the surface. Its validity is better matched when the spike is small in stress amplitude and not so deep in comparison to the deeper part of the profile.

In addition to the generic power 'n' profile, the important difference between this disclosure and the prior art methods is how the FSM_DOL is computed and how the $$CS_{knee} = \sigma_1'\left(\frac{K_2 \times FSM\_DOL}{L}\right)$$

is found using the "last common mode" measured, referring to the highest-order guided mode that appears both in the TM and the TE spectrum. In an example, if each of the TM has 3 modes and the TE spectrum has 3 modes, then the last common mode is assigned to the third mode of each spectrum, when modes are ordered by descending effective index. If the TM spectrum has 3 modes and the TE spectrum has 2 modes, then the last common mode is the second mode in each spectrum when the modes in each spectrum are ordered by descending effective index.

Figure 7A:
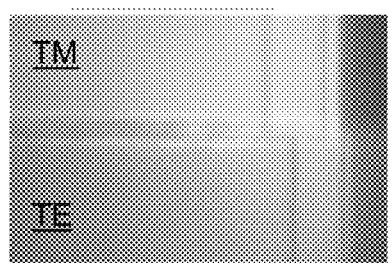
FIGS. 7A through 7C show a series of mode spectra as measured on an example chemically strengthened glass substrate, wherein the measurements were made at different diffusion times.
Figure 7B:
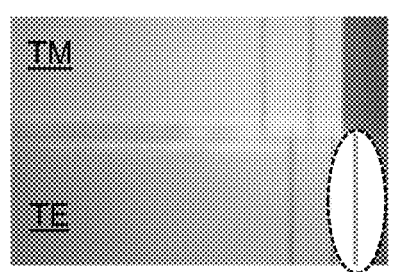
Figure 7C:
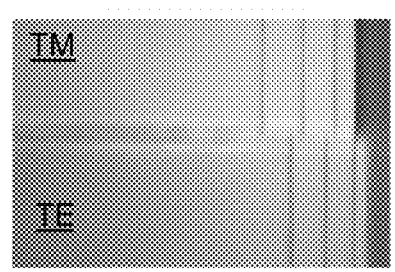

This has direct correspondence to the range of value in which a measurement is possible with reasonable noise and certainty. This is illustrated in FIG. 7A through 7C, which respectively show example mode spectra during the formation of a chemically strengthened glass substrate. The mode spectra were taken after diffusion for 1.1 h, (FIG. 7A) 2.2 h (FIG. 7B) and 3.8 h (FIG. 7C) in a bath composed of 51 wt % $KNO_3$ and 49% $NaNO_3$ at a temperature of 380 C.

The wavelength of the measurement light was 598 nm using a prism coupler system and camera. It can be observed that, depending on the diffusion time. a "new mode/fringe" starts to appear at the edge of the screen. This leads to noise in the image and an unstable determination of the transition between the spike and the long tail of the stress profile. This point is referred as the boundary/continuum or "knee point" due to the inflection on the stress curve it represents, being illustrated in FIGS. 3A and 3B as the position where the index $n^{TE}_{knee}$ and $n^{TM}_{knee}$ can be found.

FIG. 7A shows 2 fringes only. FIG. 7B shows a transition region TR between the the $2^{nd}$ and $3^{rd}$ fringes with a mode appearing in the boundary. FIG. 7C shows 3 fringes only. The concept here is to check the stability of the measurement regardless of accuracy when one uses all modes plus the boundary/continuum or knee point (known as the "chemical mode") in comparison when one measures only using all the known modes in particular using the 'last common mode/ fringe' to determine the FSM_DOL and $CS_{knee}$ (the "thermal mode, as described above).

Figure 8A:
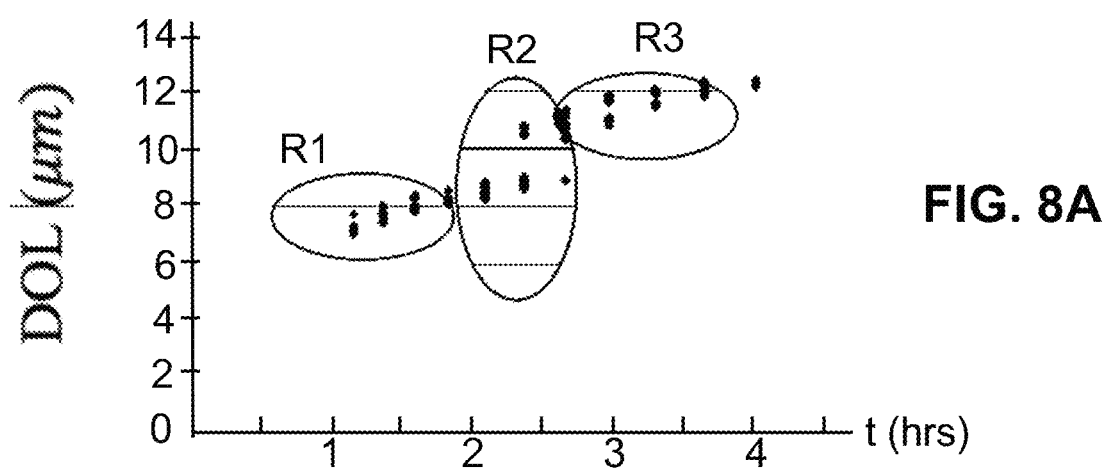
FIGS. 8A and 8B are plots of measured DOL (μm) vs. time, where region R1 shows the measurement based on two fringes (TM mode) at 589 nm, region R2 shows the transition between using three fringes (TM mode) at 589 nm, and region R3 shows the measurement using three fringes (TM mode) at 589 nm.
Figure 8B:
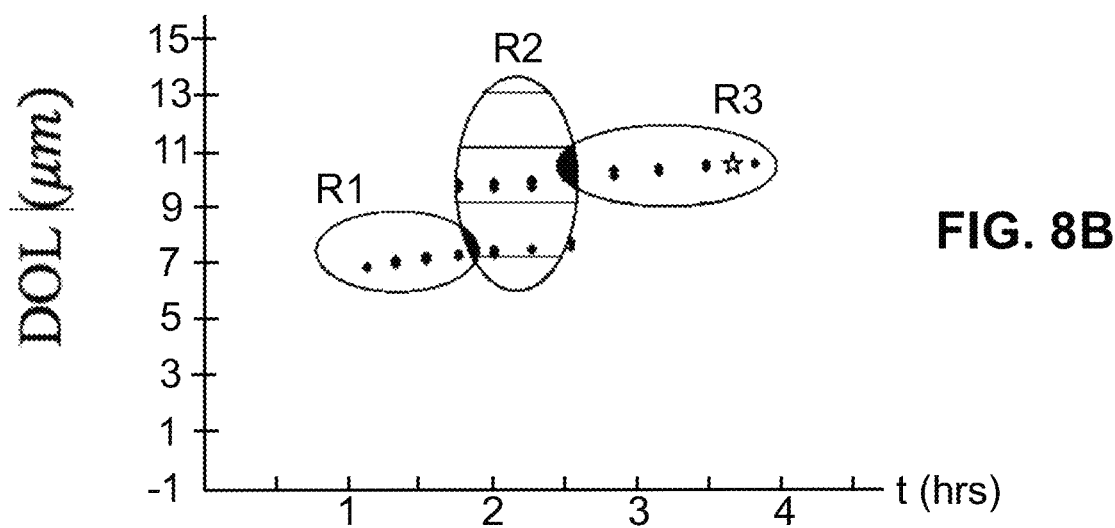

By performing several measurements in a time series of samples described above, significant trends can be observed. FIGS. 8A and 8B are plots of the depth of layer DOL (nm) versus time (hrs). In the plots, the region R1 shows the measurement based on two fringes (TM mode) at 589 nm, region R2 shows the transition between using three fringes (TM mode) at 589 nm, and region R3 shows the measurement using three fringes (TM mode) at 589 nm. FIGS. 8A and 8B show a time series of measurement of the depth of layer DOL (FSM_DOL) of the spike using the aforementioned "chemical mode" or "'all mode fringes" plus the separation between last fringe and knee point are used in computation (FIG. 8A) and the "thermal mode" or "all mode fringes" only are used in computation (FIG. 8B), which is limited by the last fringe.

FIGS. 8A and 8B allow one to clearly observe the regions R1 and R3 that provide a relatively stable measurement for FSM_DOL where the measured FSM_DOL does not oscillate (here there is no mode coming in the continuum region). There is however a region R2 where the FSM_DOL oscillates due to the fact that sometimes one computes an extra mode in the continuum region of the mode spectrum.

For our purposes, regions with 2 or more modes are acceptable but in practice we are interested in the case for diffusion times of T~3.5 hours as set-point. In this case, one can further see that when measuring using only 'all the fringes' and not including the spacing between the last known fringe and the continuum (see 54TE, 54TM of FIG. 6B), the FSM_DOL measurement has less of a spread (i.e., a smaller standard deviation). Therefore, it can provide means to control a process more robustly and identify the location of these stable measurement regions R1 and R4 more efficiently.

Figure 9A:
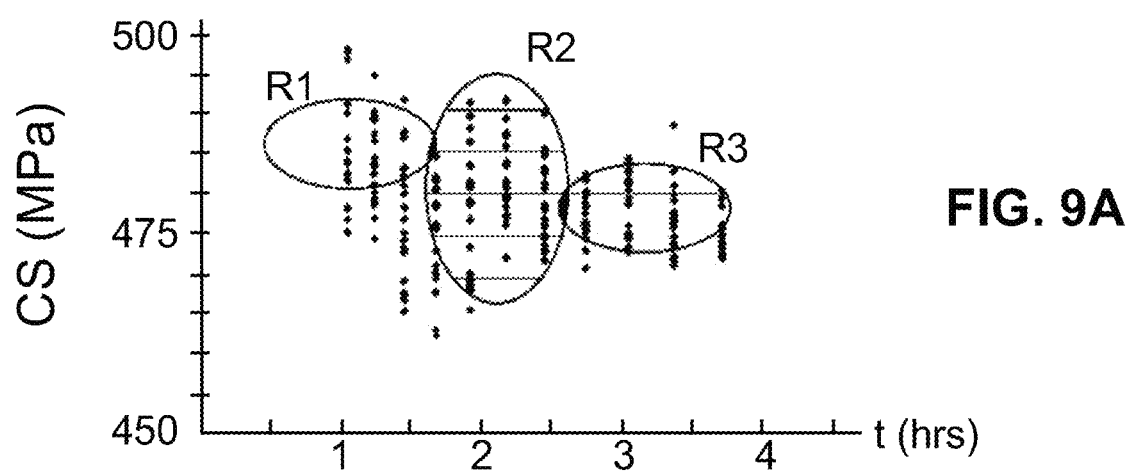
FIGS. 9A, 9B and FIGS. 10A, 10B are plots of the measured compressive stress CS (MPa) versus time in hours (hrs) and showing the same regions R1, R2 and R3 as FIGS. 8A and 8B.
Figure 9B:
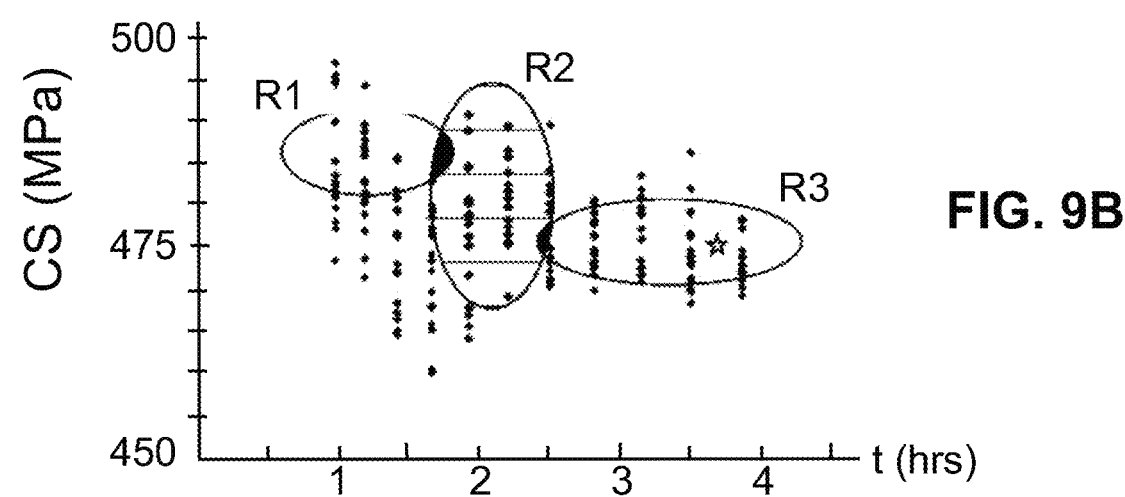

FIGS. 9A and 9B are similar to FIGS. 8A and 8B and are plots of the compressive stress at surface CS (MPa) versus time. The plot of FIG. 9A uses the chemical mode or "all mode fringes" plus the separation between last fringe and the knee point in computation in comparison to FIG. 9B, which uses the thermal mode or "all mode fringes" only, with the computation being limited by the last fringe. In this case, large changes in values are not expected because only the first 2 fringes are used in the computation of the CS, and this is indeed what is observed.

Figure 10A:
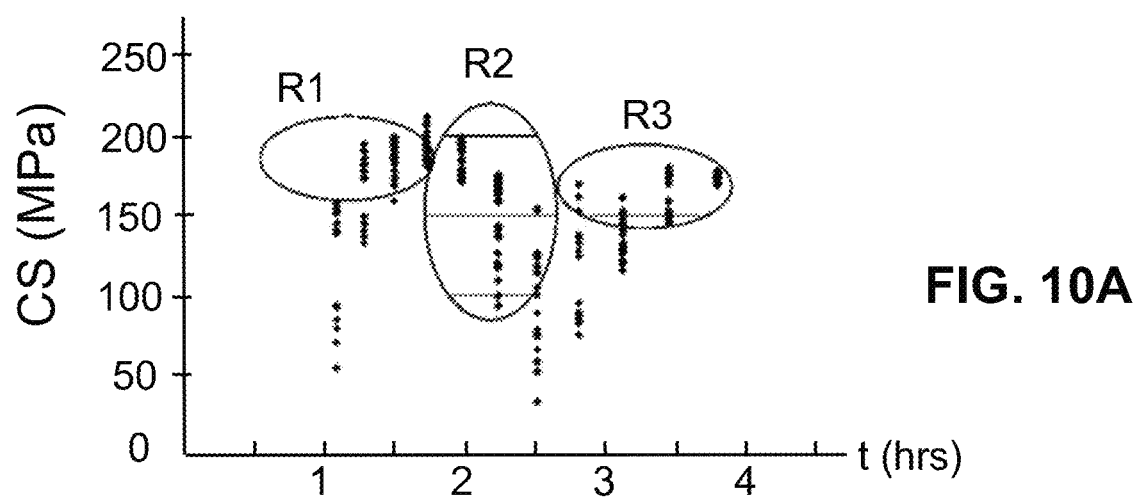
Figure 10B:
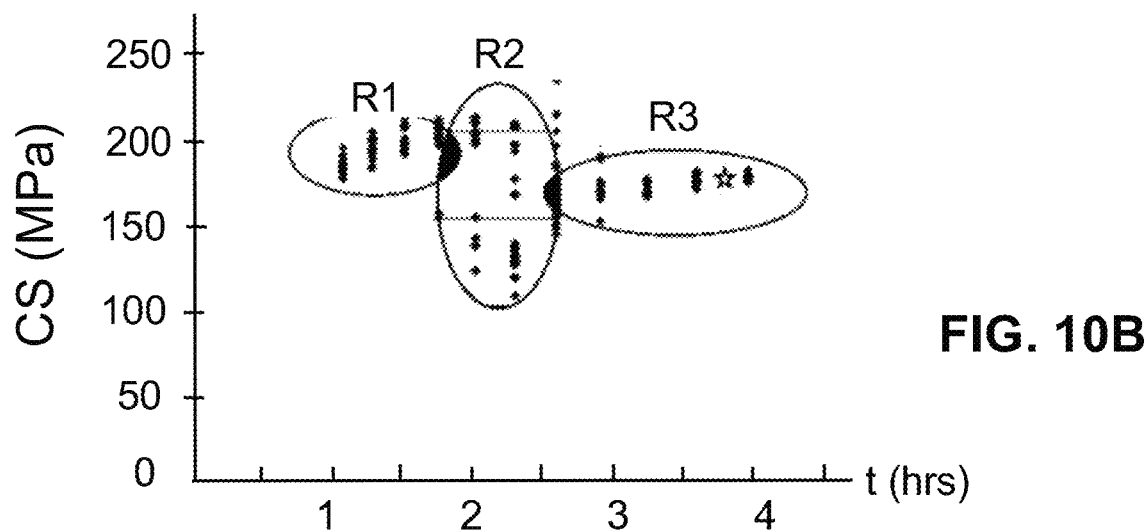

FIGS. 10A and 10B are similar to FIGS. 9A and 9B. FIG. 10A uses the chemical mode or the boundary/continuum or knee point to compute the stress at the knee. FIG. 10B uses the thermal mode or the "last common mode" and not the knee point to compute the local stress being multiplied by a scaling constant to estimate the approximated stress at the knee.

In this case, it is important to mention that the in the "chemical mode" of the FSM-6000 prism-coupling stress meter, critical angle and its corresponding effective index are found by the position of the identified and saved boundary between the TIR region having the discrete modes, and the continuum of radiation modes coupled to the deep region, and the knee stress can be calculated by:

$$\sigma_{knee} = \frac{(n_{crit}^{TE} - n_{crit}^{TM})}{SOC}, \quad (9)$$

The "thermal mode" of the FSM-6000 instrument computes abstract stress values corresponding to each mode common to the TM and TE spectrum. These abstract stress values are obtained by dividing the difference of the effective indices of the TM and the TE mode in question by the stress-optic coefficient (SOC). The present inventors have determined that the abstract stress corresponding to the "last common mode" can be used to compute the stress at the knee, because there is substantial spatial overlap between the spatial distribution of the last mode guided in the spike, and the region of the knee in the stress profile. In one relatively crude embodiment, the knee stress can be approximately obtained by multiplying the surrogate last-common-mode stress by a scaling factor $K_3$. This calibration factor is found empirically by comparing the surrogate stress of the last common mode with the actual knee stress measured by independent means (for example, by the refractive-near-field technique, by polarimetric stress measurements, or by computer simulations of diffusion and the resulting stress distribution).

The experimental factor $K_3$ needs to be acquired via measurement at the "knee point" and calculation of the surrogate stress of the last common mode to generate a scaling that can be used for a particular range of recipes.

In the particular case here for diffusion times of about T=3.5 h, this scaling factor is $K_3$=0.646. Therefore, using the "last common mode," one can compute the stress at the knee and use this information in the previous formulas as given by:

$$\sigma_{knee} = K_3 \frac{(n_{last\_node}^{TE} - n_{last\_node}^{TW})}{SOC} = \sigma_1' \left( \frac{K_2 \times FSM\_DOL}{L} \right) \quad (10)$$

The last step is to find the $K_2$ factor. In an example, this is done experimentally by measurements of the stress profile by other means (e.g., via destructive measurements) and then comparing to the value found using the FSM_DOL. As mentioned before, this value of $K_2$ is between 1 and 3. Therefore $K_2$ is the scaling of the correct position of the knee as a function of the measured FSM_DOL for a certain range of samples. As previously mentioned, since the deep part of the profile is slow varying, a certain level of inaccuracy here will not result in large errors.

Finally, it is also known that the CS measured by the FSM is an approximation considering a linear diffusion profile. In some cases, if a more accurate determination of the CS is needed that can be corrected by another correction factor $K_4$. This factor is usually quite close to 1. In practice, it was found that $K_4$ of about 1.08 leads to more accurate representations of the CS in a significant range. Therefore, if needed one can also use for more accuracy on CS determinations, the relationship:

$$CS_{corr} = K_4 \times CS \quad (11)$$

Examples of the use of all the above formulas for the "last know mode" method is set forth in Table 1 in FIG. 11. In Table 1, the formulas were used to generate all of the critical parameters of the stress profile for a range of timed glass samples. Constants used were: n=2 (power-law profile on parabolic deep part PDP), $K_1$=1.25, $K_2$=2, $K_3$=0.646 and $K_4$=1 (not corrected for CS). The samples were prepared in a bath composed of 51 wt % $KNO_3$ and 49 wt % $NaNO_3$ at a temperature of 380 C.

In another embodiment of the method, the weight gain of a sample as a result of ion exchange is used in combination with the prism-coupling measurement. The weight gain may be used to verify that enough Na+ ions have exchanged for Li+ ions such that the use of the parabolic-profile model is valid for quality control. For the purpose, a target acceptable weight gain range is prescribed for the ion exchange based on the total surface area of the sample and the sample thickness. The weight of representative samples is measured before and after ion exchange, and the quality-control prism-coupling measurements are considered valid if the measured weight gain per sample falls in the target range.

In another embodiment of the method, advantage is taken of the precise control of the sample shape, and of individual-sample thickness measurements that are common in some production processes. In this case it is possible to verify that the sample has had adequate weight gain by simply measuring the sample thickness with high precision (such as +/−1 micron), and by measuring the post-ion exchange weight of the sample. From the known shape specification, the measured thickness, and the known density of the pre-ion-exchanged glass, the weight of the pre-ion-exchanged sample is calculated.

A correction factor may be applied that accounts for a typical volume change as a result of ion exchange. The weight gain then is estimated by subtracting from the measured post-ion-exchange weight the estimated pre-exchanged weight. If the weight gain falls within the target range, the profile is deemed adequately represented by the quality-control model profile, and the prism-coupling QC measurement is considered valid.

Another embodiment of the stress-slope method for indirect measurement of $CS_k$ offers substantial improvement in the precision of measurement of $CS_k$ over the embodiment using the slope of the spike measured from only the effective indices of the first two guided modes and the DOL of the spike. The original method described above suffered from precision limitations associated with normal variability in the detection of the positions of the fringes in the coupling spectrum corresponding to these modes.

The present improved method utilizes three or more modes for at least one polarization, when available, to calculate the stress slope with substantially improved precision, thus allowing much more precise calculation of $CS_k$. The method works well because image-noise-induced errors in neighboring fringe spacings are anti-correlated, and get substantially eliminated when a single linear fit through three or more fringe positions is utilized.

The method substantially improves the precision of the $CS_k$ measurement and the CS measurement for a substantially linear spike by using at least three fringes in at least one of the two polarizations (TM and/or TE) (see FIG. 12 and Tables 2A and 2B, introduced and discussed below). Spike shapes that deviate slightly-to-moderately from a substantially linear shape can still benefit an improvement in precision, although a correction for the shape deviation from linear may be required in order to obtain the most accurate $CS_k$ values. This type of correction can be obtained, for example, by a one-time calibration for each specific spike shape. The calibration may involve identifying a fraction of the DOL at which $CS_k$ is calculated, where the fraction can be greater or smaller than 1 (the fraction being equal to 1 for a strictly linear spike).

Method of Calculating Knee Stress

The following describes an example method of calculating the knee stress $CS_k$ with reduced susceptibility to the noise of any particular mode by a slope fit method that utilizes several modes at once.

The following equation is used in the method and is for a linear profile that relates two arbitrary modes m and/confined within the spike, their effective indices being $n_m$ and $n_l$, and the index slope $s_n$:

$$(n_m+n_l)^{1/3}(n_m-n_l)=s_n^{2/3}(3/16\lambda)^{2/3}[(4l+3)^{2/3}-(4m+3)^{2/3}]$$

The above equation can be used to perform a linear regression, or an evaluation of $s_n$ from each pair of modes, and calculate an average for $s_n$. Mode counting starts from m=0 for the lowest-order mode. The parameter $\lambda$ is the optical wavelength used for the measurements.

An example of the method of calculating the knee stress thus includes the following steps:

1) Set a reference index to get all measured modes as actual effective indices. A good reference index is usually the index corresponding to the TM critical-angle transition. For Zepler and FORTE glasses, this index is very close to the original substrate index, which is usually specified.
2) Measure all mode effective indices, $n_m$, m=0, 1, 2, . . . , for each polarization, using the angular prism-coupling spectrum of guided modes.
3) If desired, assume that $n_m+n_l$ hardly changes, and assign it as a constant equal to $2\bar{n}$.
4) For each pair of integers m, l≥0, calculate $$B_{ml}=\frac{\left(\frac{3}{16}\lambda\right)^{\frac{2}{3}}\left[(4l+3)^{\frac{2}{3}}-(4m+3)^{\frac{2}{3}}\right]}{(n_m+n_l)^{\frac{1}{3}}} \approx \frac{\left(\frac{3}{16}\lambda\right)^{\frac{2}{3}}\left[(4l+3)^{\frac{2}{3}}-(4m+3)^{\frac{2}{3}}\right]}{(2\bar{n})^{\frac{1}{3}}}$$

5) Perform a linear regression of the equation $y_{ml} \equiv n_m - n_l = SB_{ml}$, to find a capital slope S.
6) If desired, check if the quality of the linear regression is adequate (e.g., $R^2$ is higher than a minimum requirement).
7) Find the index slope using $s_n = S^{3/2}$
8) Find the surface index for the purposes of the subsequent knee-stress calculation using:

$$s_n = \frac{16}{3(4m+3)\lambda}(n_{surf}+n_m)^{\frac{1}{2}}(n_{surf}-n_m)^{\frac{3}{2}}$$

$$n_{surf} = n_m + \frac{s_n^{\frac{2}{3}}}{(2\bar{n})^{\frac{1}{3}}}\left[\frac{3(4m+3)\lambda}{16}\right]^{\frac{2}{3}}$$

9) If higher accuracy is desired, replace $2\bar{n}$, for each pair of modes with the actual sum of the measured values, $n_m+n_l$, as mentioned earlier
10) For the calculation of $2\bar{n}$, used in the calculation of $n_{surf}$, optionally use an iterative procedure, where in the first step we use $2n_0$, and on the second iteration, use $n_0+n_{surf}^{(0)}$, e.g., use the estimated surface index form the first iteration to calculate the average of the surface and the first mode. For faster calculation, use:

$$2\bar{n} \approx n_0+n_0+1.317(n_0-n_1) \equiv 2n_0+1.317(n_0+n_1)$$

11) Calculate the surface CS for the purposes of finding the knee stress: $CS=(n_{surf}^{TE}-n_{surf}^{TM})/SOC$
12) Calculate the stress slope for the purposes of finding the knee stress:

$$s_\sigma = \frac{s_n^{TE}-n_n^{TM}}{SOC}$$

13) Find the DOL from the upper TM spectrum for higher precision
14) Calculate the knee stress: $\sigma_{knee}=CS+s_\sigma \times DOL$
15) If the deeper end of spike differs somewhat from linear as truncated on the deep side, then apply a correction factor: $\sigma_{knee}=CS+F \times s_\sigma \times DOL$, where F is the correction factor, usually between about 0.4 and 1, but for spikes having regions of negative curvature it could exceed 1. The correction factor can be calculated by accounting for the actual concentration profile of potassium (K) measured by secondary-ion mass spectroscopy (SIMS), glow-discrharge emission spectroscopy (GDOES), or electron microprobe, or it can be found empirically by comparing measured knee stresses to the equation above and fitting the value of F that makes them agree.

Clearly the above method can be applied to either or both of the TM and TE index profiles of the potassium-enriched spike, to improve the precision of CS and $CS_k$. The improvement is most significant when it is applied to both the TM and the TE spectra, but it could be used in cases where one of the spectra only has 2 guided modes (for example the TE spectrum), in which case the linear regression is applied only to the spectrum having at least 3 guided modes. Furthermore, it can clearly be applied using in general a different number of TM and TE modes, although the accuracy might be highest when the same number of TM and TE modes are used.

The data from application of the two major embodiments of the slope method for indirect $CS_k$ calculation to actual prism-coupling measurements of several samples covering a range of different DOL are shown in Tables 2A and 2B, below. Table 2A shows the results of the prior-art method of calculation employing two modes while Table 2B shows the results of the improved method of calculation as disclosed herein that uses additional modes.

TABLE 2A

| Single mode pair stress slope method | |
|---|---|
| CS | $CS_K$ |
| 528.2 | 143.9 |
| 519.1 | 136.2 |
| 520.4 | 130.3 |
| 515.7 | 126.7 |
| 512.9 | 112.9 |
| 519.3 | 122.3 |
| 509.5 | 121.2 |
| 513.1 | 117.9 |
| 517.7 | 119.7 |
| 514.2 | 120.8 |
| 515.3 | 123.1 |
| 515.6 | 127.4 |
| 515.9 | 118.5 |
| 517.8 | 128.7 |
| 515.5 | 125.0 |
| Standard Deviation | |
| 4.3 | 7.8 |

TABLE 2B

Single mode pair stress slope method

| CS | $CS_K$ |
|---|---|
| 525.4 | 144.6 |
| 516.4 | 142.5 |
| 517.5 | 146.0 |
| 513.2 | 143.8 |
| 509.8 | 149.1 |
| 516.4 | 148.3 |
| 506.9 | 142.6 |
| 511.3 | 144.6 |
| 514.8 | 148.7 |
| 512.1 | 144.9 |
| 512.9 | 144.8 |
| 513.1 | 143.3 |
| 513.8 | 146.6 |
| 515.4 | 144.1 |
| 513.3 | 143.9 |
| Standard Deviation | |
| 4.1 | 2.1 |

Figure 12:
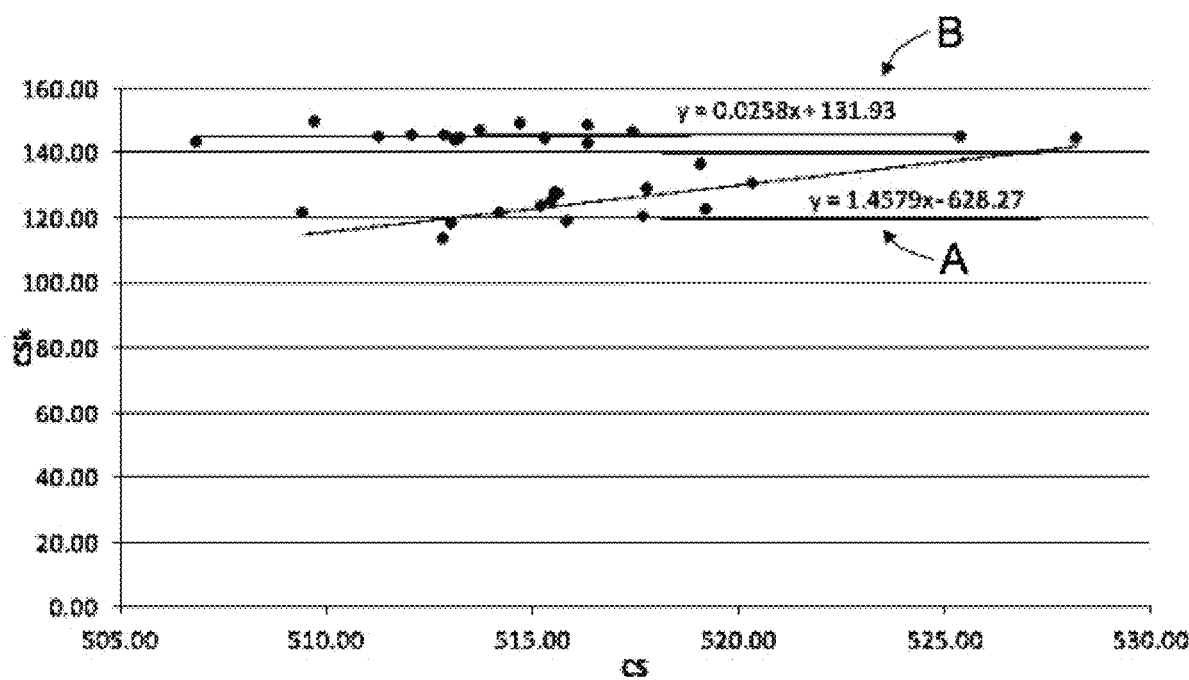
FIG. 12 shows a reduced range and reduced dependence of $CS_k$ on CS for measured samples covering a range of DOL after applying an improved algorithm for slope extraction (fitted curve B) based on using three or more optical modes per polarization as opposed to two optical modes per polarization (fitted curve A)

From the data of Tables 2A and 2B, plots of CS vs extracted $CS_k$ using the two methods from first two modes only (fitted curve A), and from using all available modes for slope calculation (fitted curve B) are shown in FIG. 12. The last row in Table 2B shows a substantially reduced standard deviation in the indirect measurement of $CS_k$ when the slope is extracted from using all the modes (three or more), rather than only the two lowest-order modes as used in the method of Table 2A (fitted curve A).

The data in FIG. 12 for the same improved method has a substantially smaller spread for $CS_k$, indicative of the reduced standard deviation. The data also shows a much smaller dependence on CS, suggesting that the extraction of $CS_k$ from only the first two fringes is subject to measurement errors that tend correlate $CS_k$ with CS.

Two other embodiments of the method offer a substantial improvement in the accuracy of measurement of $CS_k$ based on the other indirect method disclosed earlier, i.e., the method that uses the birefringence of the highest-order guided mode of the spike to estimate $CS_k$. The highest-order guided mode has effective index only slightly higher than the effective index corresponding to the depth at which the knee of the stress profile occurs. Thus, the birefringence of that mode is significantly affected by the knee stress. If the spike CS and DOL are kept constant, then the knee stress $CS_k$ would be essentially the sole driver of changes in the birefringence of the highest-order spike mode.

The method described above calculates the knee stress $CS_k$ as a fraction of the birefringence of the highest-order spike mode. A problem with this method can occur when the CS and DOL of the spike are allowed to vary moderately or significantly by a relatively broad product specification, as typical for chemically strengthened cover glasses.

The two improved embodiments of the method for calculating the knee stress $CS_k$ disclosed below correct for the effects of varying CS and DOL of the spike on the birefringence of the surrogate guided mode so that the indirectly recovered value of $CS_k$ is more accurate. Improvement of the accuracy of $CS_k$ measurements is sought by correcting for significant distortions of indirectly-extracted $CS_k$ values by the last-fringe method (birefringence of the highest-order guided mode acting as a surrogate for the knee-stress-induced birefringence).

In one aspect of the method, a derivative of the birefringence of the chosen surrogate guided mode is calculated with respect to deviations of the CS, DOL, and $CS_k$ from their nominal values for the target product. Then $CS_k$ is calculated from the measured surrogate-mode birefringence, after applying corrections associated with the product of these calculated or empirically extracted derivatives, and the corresponding measured deviations of CS and DOL from the target values.

In an example, the spike shape may be assumed to have a linear distribution from the surface to the depth of the knee. This is a good approximation for a single-step process. An erfc-shaped spike can be considered a good approximation for a two-step process, where the first-step uses a lower substantially nonzero potassium concentration in the bath, and forms a substantially lower CS than the second step, and where the second step has a substantially shorter ion exchange time at approximately the same or lower temperature than the first step. The specific shape of the profile does not affect the method of correction, only the absolute values of the correction factors.

In the present example, the last-fringe birefringence was calculated by using the linear-spike approximation. The fabrication process involves a sample of 0.5 mm thick Corning 2321 glass subjected to ion exchange at 380 C for approximately 1.6 hours in a mixture having approximately 20% $NaNO_3$ and 80% $KNO_3$ by weight. The nominal CS for the target is 675 MPa and the nominal DOL is 9 microns.

Table 3 is presented in FIG. 13 and shows the calculated effective indices of the three guided modes for both the TM and TE polarizations for several different assumed values of $CS_k$, CS, and DOL. Effective indices can be calculated numerically, e.g., by a mode solver that numerically solves the wave equation, or by a transfer-matrix approach, for example. Such methods are well known in the art.

The eighth column shows the birefringence of the third guided mode (mode indexing counts from 0, so the third guided mode is TM2/TE2). The ninth column shows the abstract compressive stress Sn2 corresponding to the birefringence of the highest-order guided mode (in this case, the third). This abstract compressive stress is obtained by dividing the mode birefringence by the stress-optic coefficient SOC.

The rightmost column shows the calculated change in the calculated abstract compressive stress by a unit change in the corresponding parameter (i.e., a 1 MPa change in $CS_k$, a 1 MPa change in surface CS, or a 1 micron change in DOL). These can be used approximately as the derivatives of the abstract compressive stress with respect to changes of the driving parameters. It can be seen from Table 3 that the so-calculated derivatives may be slightly different on the side of increasing a parameter than on the side of decreasing of the same parameter. This is due to using a finite interval for calculating the derivatives. The difference can be decreased if a smaller interval is used for the estimates. In practice, the average derivative from the positive and negative side of the parameter change may be used over the entire interval to provide a fairly good correction.

If the surrogate abstract mode compressive stress calculated from the birefringence of the highest-order guided common mode is labeled $CS_{sur}$, then the corrected value of knee stress can be calculated using the measured values of CS, DOL, and $CS_{sur}$, and using the nominal values for CS, DOL, $CS_k$ and $CS_{sur}$. Generally, the calculation can use the form $$CS_k = CS_k^{nom} + \frac{(CS_{sur} - CS_{sur}^{nom}) - CorrCS - CorrDOL}{\frac{dCS_{sur}}{dCS_k}}$$

where the corrections CorrCS and CorrDOL are calculated from the product of deviations of $CS_{sp}$ and $DOL_{sp}$ from their nominal values, and the corresponding sensitivities of the surrogate stress $CS_{sur}$ to changes in $CS_{sp}$ and $DOL_{sp}$. Note that in the present disclosure, when CS is used without any subscript, it means the surface compressive stress of the spike $CS_{sp}$. A simple embodiment of the above method is using the equation:

$$CS_k = CS_k^{nom} + \frac{(CS_{sur} - CS_{sur}^{nom}) - (CS - CS^{nom})\frac{dCS_{sur}}{dCS} - (DOL - DOL^{nom})\frac{dCS_{sur}}{dDOL}}{\frac{dCS_{sur}}{dCS_k}}$$

In the above example, the equation reduces to:

$$CS_k = 95 + \frac{(CS_{sur} - 348.2) - (CS - 650)0.76 - (DOL - 9.0)47.7}{0.525}$$

The above use of linear relationship between the deviations of $CS_{sp}$ and $DOL_{sp}$ from their nominal values, and the corresponding corrections CorrCS and CorrDOL makes $CS_k$ susceptible to increased standard deviation when the measurements of $CS_{sp}$ and/or $DOL_{sp}$ are subject to substantial random error (noise). In some cases this increased standard deviation can be problematic. Limiting the amount of correction by using a nonlinear relationship between each correction and the corresponding deviation in $CS_{sp}$ or $DOL_{sp}$ from its nominal value can help stabilize the calculated $CS_k$. In an example, the corrections can be calculated by the following:

$$CorrCS = \Delta_1 \times \tanh\left(\frac{\frac{dCS_{sur}}{dCS_{sp}}(CS_{sp} - CS_{sp}^{nom})}{\Delta_1}\right)$$

And $$CorrDOL = \Delta_2 \times \tanh\left(\frac{\frac{dCS_{sur}}{dDOL_{sp}}(DOL_{sp} - DOL_{sp}^{nom})}{\Delta_2}\right)$$

Where $\Delta_1$ and $\Delta_2$ are limiting values of the corrections, preventing over-compensation due to noise in the $CS_{sp}$ and $DOL_{sp}$ values.

In another embodiment of the method, the factor $K_3$ used to relate the sought knee stress $CS_k$ and surrogate stress (calculated from the birefringence of the last guided mode), is allowed to vary with the surface CS and the spike DOL, so that the extracted value of $CS_k$ from measurements of the surrogate stress can better match the actual knee stress over a variety of CS and DOL combinations.

In an example, the CS and DOL were varied slightly in simulations of the optical modes of a chemically strengthened sample with the knee stress in the vicinity of 150 MPa, CS in the vicinity of 500 MPa, and DOL in the vicinity of 10 microns. The knee stress, which was input in the simulations, was then divided by the surrogate abstract mode stress that was calculated by the simulation, to find how the factor $K_3$ varied with CS and DOL.

Figure 14A:
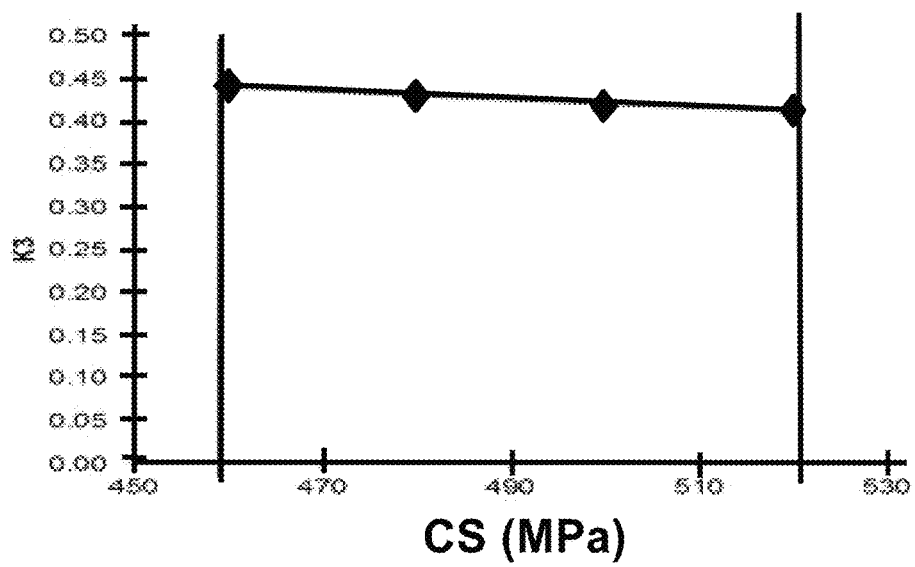
FIG. 14A shows a dependence of a knee-stress scaling factor $K_3$ on the compressive stress CS for an example simulated ion exchanged Li-containing glass, for the purpose of applying a dynamically adjusted CS-dependent factor for correcting systematic error of $CS_k$ measurement in one embodiment, the systematic error resulting from $K_3$ being assumed constant.

FIG. 14A shows a calculated dependence of $K_3$ on CS (i.e., $K_3$ vs. CS (MPa)). The vertical lines show a range of CS over which $K_3$ can be approximated as constant for the purposes of $CS_k$ calculations in this example. In other cases with substantially steeper spikes (e.g., slope in the vicinity of 100 MPa/micron), the range of CS over which $K_3$ can be approximated as constant would be narrower.

Figure 14B:
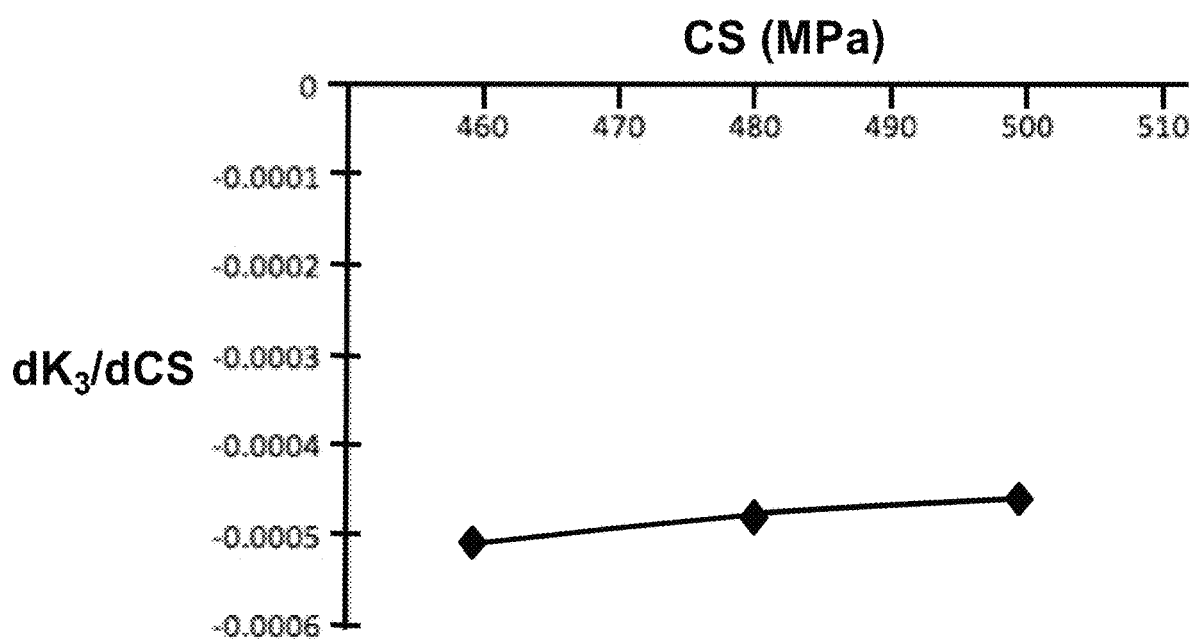
FIG. 14B shows the derivative of scaling factor $K_3$ with respect to CS ($dK_3/dCS$) and the minor dependence of that derivative on the CS value, for the purposes of correcting systematic error in $CS_k$ in one embodiment where the systematic error results from $K_3$ being assumed constant.

FIG. 14B shows the derivative of $K_3$ with respect to CS ($dK_3/dCS$) calculated from the same data. It can be used to calculate a $K_3$ value from a nominal $K_3$ value obtained during a calibration measurement of a stress profile (e.g., by polarimetry or refractive-near-field measurements) by applying a correction.

Figure 15:
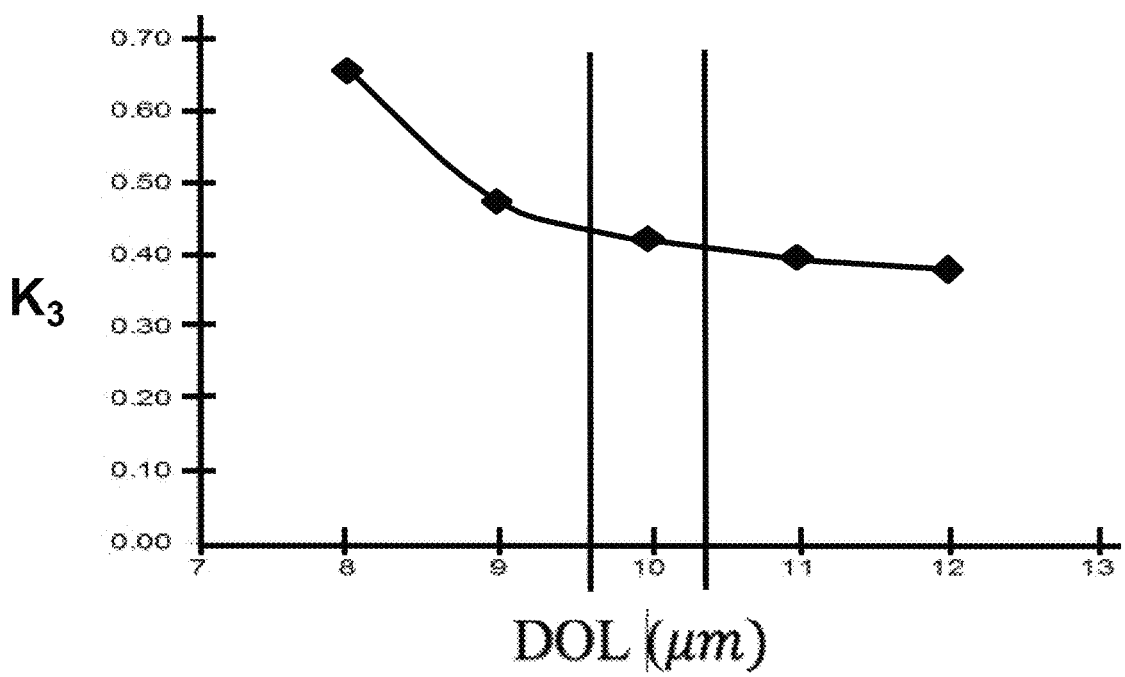
FIG. 15 shows dependence of the scaling factor $K_3$ on DOL, for simulated profiles covering a range of DOL, for the purpose of correcting a systematic error in $CS_k$ resulting from assuming that $K_3$ is constant and independent of DOL.

FIG. 15 shows the dependence of $K_3$ on the DOL. At smaller DOL values than about 9.5 microns the dependence becomes steeper, presumably due to the third TE mode transitioning from a guided mode to a leaky mode. Usually the measurement is not in the sweet spot in that case, and such a region would be avoided.

Figure 16:
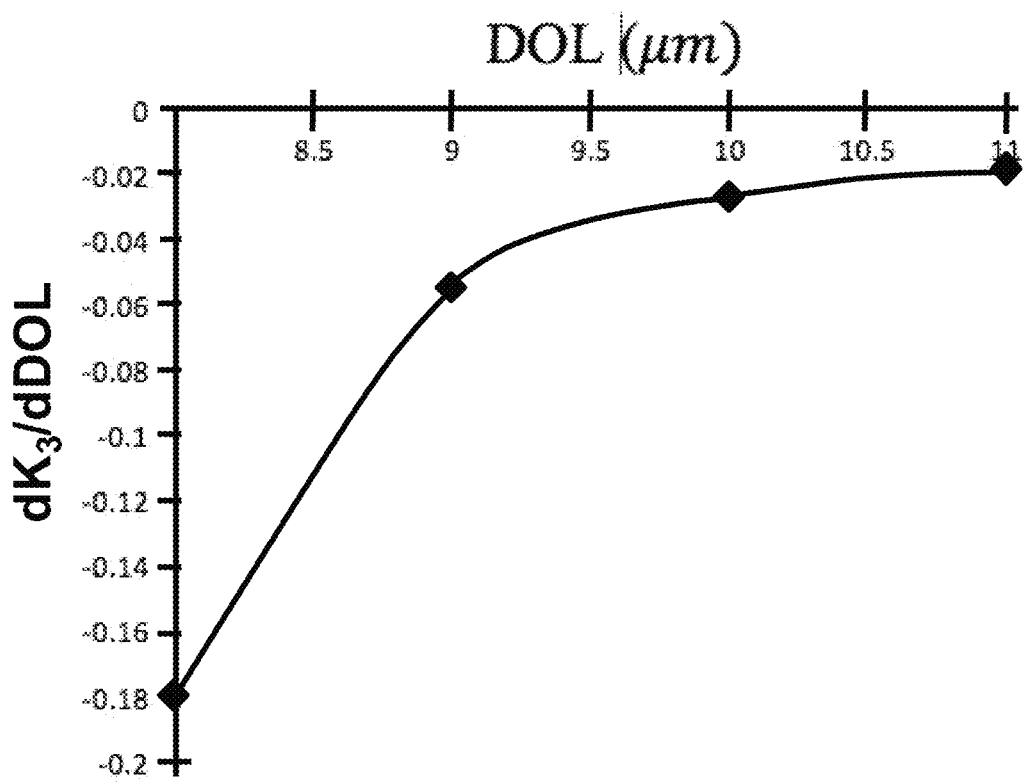
FIG. 16 shows a derivative of the scaling factor $K_3$ with respect to DOL ($dK_3/dDOL$) having a region of relatively small and little changing derivative, and a region of fast-changing derivative, growing substantially in absolute value.

FIG. 16 shows a derivative of the scaling factor $K_3$ with respect to DOL ($dK_3/dDOL$) having a region of relatively small and little changing derivative, and a region of fast-changing derivative, growing substantially in absolute value. Operating in the region where the derivative of $K_3$ with respect to DOL is small by absolute value and changing little is preferred for the embodiments involving indirect measurements of $CS_k$ based on the birefringence of the last guided mode.

In an example, the corrected value of $K_3$ can be calculated as follows:

$$K_3(CS, DOL) = K_3^{nom}(CS = CS^{nom}, DOL = DOL^{nom}) + (CS - CS^{nom})\frac{dK_3}{dCS} + (DOL - DOL^{nom})\frac{dK_3}{dDOL}$$

In another example, the value of $K_3$ can be tabulated for a matrix of CS and DOL combinations, and read out during measurements by an algorithm selecting the closest CS/DOL combination to the measured values of CS and DOL.

In another embodiment of the method, the value of $K_3$ need not be corrected. Instead, the range of combinations of CS, DOL, and uncorrected $CS_k$ can be separated in several regions, such that combinations having high CS and DOL, and low $CS_K$ can be rejected during quality-control measurements. This account for the observation that high CS and DOL both tend to raise the indirectly-measured $CS_K$ by the highest-guided-mode surrogate method.

In one example, a process space (process window) is defined by the product of the CS and DOL specifications. This process space is then split into two or more regions, preferably in parallel to the diagonal relating the point (CSmax, DOLmin) with the point (CSmin, DOLmax). Then for each region, a different lower limit of $CS_K$ is used as a reason to reject a part, with the so required $CS_K$ lower limit generally increasing with increasing CS and increasing DOL. In another example, the CS/DOL process space can be split into two or more sub-regions by curves corresponding to the condition CS*DOL=const, or $(CS-CS_K^{nom})*DOL=$const.

It will be apparent to those skilled in the art that various modifications to the preferred embodiments of the disclosure as described herein can be made without departing from the spirit or scope of the disclosure as defined in the appended claims. Thus, the disclosure covers the modifications and variations provided they come within the scope of the appended claims and the equivalents thereto.

What is claimed is:

1. A method of characterizing a stress profile of a chemically strengthened glass substrate formed by the in-diffusion of alkali ions and having an upper surface and a body, a shallow spike region of stress immediately adjacent the upper surface and a deep region of slowly varying stress within the body and that intersects the spike region at a knee, wherein the method comprises:

measuring a TM mode spectrum and a TE mode spectrum of the glass substrate, wherein the TM mode spectrum and the TE mode spectrum each include mode lines associated with the spike region, a portion of total-internal reflection (TIR), a portion of partial reflection where there is optical coupling into the deep region of the substrate, and a transition between the two portions associated with a critical angle;

determining a surface compressive stress $CS_{sp}$ of the spike using either at least one of the TM and TE mode spectra or a measurement of a surface concentration of at least one type of alkali ion that resides adjacent the surface;

determining a stress slope $s_o$ of the spike using a plurality of the mode lines of the spike region of at least one of the TE and TM mode spectra;

calculating a depth of layer $DOL_{sp}$ of the spike using the modes lines of at least one of the TM and TE spectra; and calculating an amount of compressive stress $CS_{knee}$ at the knee using the surface compressive stress $CS_{sp}$, the stress slope $s_o$ and the spike $DOL_{sp}$ using the relationship:

$CS_{knee} = CS_{sp} + (CF)(s_o)(DOL_{sp})$ where CF is a calibration factor in the range from 0.2 to 2 in absolute value.

2. The method according to claim 1, where the alkali ions are Na and K, wherein glass substrate contains Li, and wherein the deep region of the profile is enriched with Na and the shallow region is enriched in K.

3. The method according to claim 1, wherein the determining of the stress slope $s_o$ is performed using the two lowest-order mode lines of each of the TE mode spectrum and the TM mode spectrum.

4. The method according to claim 1, wherein the determining of the stress slope $s_o$ is performed using three or more mode lines of at least one of the TE mode spectrum and the TM mode spectrum.

5. The method according to claim 1, wherein the determining of the stress slope $s_o$ is performed using either a linear regression or by an averaging process using pairs of mode lines.

6. The method according to claim 1, wherein the depth of layer $DOL_{sp}$ is calculated using only the mode lines and the transition of the TM spectrum.

7. The method according to claim 1, wherein calculating the $DOL_{sp}$ further includes using a distance between the transition and the most adjacent mode line to the transition.

8. The method according to claim 1, wherein CF is in the range from 0.5 to 2 in absolute value.

9. The method according to claim 8, where the alkali ions are Na and K, wherein glass substrate contains Li, and wherein the deep region of the profile is enriched with Na and the shallow region is enriched in K.

10. The method according to claim 8, wherein the determining of the stress slope $s_o$ is performed using the two lowest-order mode lines of each of the TE mode spectrum and the TM mode spectrum.

11. The method according to claim 8, wherein the determining of the stress slope $s_o$ is performed using three or more mode lines of at least one of the TE mode spectrum and the TM mode spectrum.

12. The method according to claim 8, wherein the determining of the stress slope $s_o$ is performed using either a linear regression or by an averaging process using pairs of mode lines.

13. The method according to claim 8, wherein the depth of layer $DOL_{sp}$ is calculated using only the mode lines and the transition of the TM spectrum.

14. The method according to claim 8, wherein calculating the $DOL_{sp}$ further includes using a distance between the transition and the most adjacent mode line to the transition.

* * * * *